(12) United States Patent
Coudray et al.

(10) Patent No.: US 9,073,867 B2
(45) Date of Patent: Jul. 7, 2015

(54) PROCESS FOR PREPARING CAPROLACTAM AND POLYAMIDES THEREFROM

(75) Inventors: Laetitia Coudray, Emeryville, CA (US); Vu Bui, Davis, CA (US); John W. Frost, Okemos, MI (US); Dirk Schweitzer, Belmont, MA (US)

(73) Assignee: Amyris, Inc., Emeryville, CA (US)

( * ) Notice: Subject to any disclaimer, the term of this patent is extended or adjusted under 35 U.S.C. 154(b) by 425 days.

(21) Appl. No.: 13/442,306

(22) Filed: Apr. 9, 2012
(Under 37 CFR 1.47)

(65) Prior Publication Data
US 2013/0085255 A1    Apr. 4, 2013

Related U.S. Application Data

(60) Provisional application No. 61/473,754, filed on Apr. 9, 2011, provisional application No. 61/473,753, filed on Apr. 9, 2011.

(51) Int. Cl.
| | | |
|---|---|---|
| C07D 223/10 | (2006.01) |
| C07C 209/48 | (2006.01) |
| C08G 69/26 | (2006.01) |
| C08G 69/28 | (2006.01) |
| C07C 231/02 | (2006.01) |
| C07C 235/74 | (2006.01) |
| C07C 235/76 | (2006.01) |
| C07C 255/04 | (2006.01) |
| C07C 255/09 | (2006.01) |

(52) U.S. Cl.
CPC .......... *C07D 223/10* (2013.01); *C07C 209/48* (2013.01); *C08G 69/26* (2013.01); *C08G 69/28* (2013.01); *C07C 231/02* (2013.01); *C07C 235/74* (2013.01); *C07C 235/76* (2013.01); *C07C 255/04* (2013.01); *C07C 255/09* (2013.01)

(58) Field of Classification Search
None
See application file for complete search history.

(56) References Cited

U.S. PATENT DOCUMENTS

| | | |
|---|---|---|
| 2,351,939 A | 6/1944 | Drossbach et al. |
| 3,152,186 A | 10/1964 | Campbell et al. |
| 3,392,222 A | 7/1968 | Cordon |
| 3,398,195 A | 8/1968 | Williams |
| 3,607,906 A | 9/1971 | Hofmann et al. |
| 3,627,736 A | 12/1971 | Raum et al. |
| 3,629,316 A | 12/1971 | Hatten et al. |
| 3,671,566 A | 6/1972 | Decker et al. |
| 3,914,217 A | 10/1975 | Smith |
| 4,263,175 A | 4/1981 | Pesa et al. |
| 4,356,124 A | 10/1982 | Pesa et al. |
| 4,599,202 A | 7/1986 | Dockner et al. |
| 4,725,542 A | 2/1988 | Barer et al. |
| 4,804,754 A | 2/1989 | De Decker et al. |
| 4,929,396 A | 5/1990 | Barer et al. |
| 5,194,577 A | 3/1993 | Chen |
| 5,218,082 A | 6/1993 | Reimann et al. |
| 5,264,571 A | 11/1993 | Fuchs et al. |
| 5,276,131 A | 1/1994 | Akkapeddi et al. |
| 5,487,987 A | 1/1996 | Frost et al. |
| 5,665,854 A | 9/1997 | Kosinski et al. |
| 5,763,561 A | 6/1998 | Keske |
| 6,291,633 B1 | 9/2001 | Nakamura |
| 6,846,868 B2 | 1/2005 | Oka et al. |
| 7,053,169 B2 | 5/2006 | Buhler |
| 7,351,820 B2 | 4/2008 | Thomissen et al. |
| 2002/0183478 A1 | 12/2002 | Fergusson et al. |
| 2004/0049006 A1 | 3/2004 | Aramaki |
| 2007/0244317 A1 | 10/2007 | Crabtree et al. |
| 2007/0254341 A1 | 11/2007 | Raemakers-Franken et al. |
| 2008/0319219 A1 | 12/2008 | Ostermaier |
| 2009/0005532 A1 | 1/2009 | Frost |

FOREIGN PATENT DOCUMENTS

| | | |
|---|---|---|
| JP | 03-2850909 | 12/1991 |
| WO | WO 91/18941 | 12/1991 |
| WO | WO 2009/153534 | 12/2009 |
| WO | WO 2010/004194 | 1/2010 |
| WO | WO 2010/063632 | 6/2010 |
| WO | WO 2010/085712 | 7/2010 |
| WO | 2010/148049 | 12/2010 |
| WO | 2010/148070 | 12/2010 |
| WO | 2010/148080 | 12/2010 |
| WO | 2010/148081 | 12/2010 |
| WO | WO 2010/148063 | 12/2010 |
| WO | 2012/141993 | 10/2012 |
| WO | 2012/141997 | 10/2012 |

OTHER PUBLICATIONS

Elvidge et al., "Polyene acids. Part VIII: The Isomeric Muconic Diamides and Mucononitriles," Journal of the Chemical Society C: Organic. p. 385-387 (1966).
Goto et al., "RhI-Catalyzed Hydration of Organonitrales under Ambient Conditions," Angewandte Chemie International Edition. 47(19): 3607-3609 (2008).
Hann et al., "5-Cyanovaleramide Production Using Immobilized *Pseudomonas chloraphis* B23," Bioorganic and Medicinal Chemistry. 7(10): 2239-2245 (1999).
Niu et al., "Benzene-Free Synthesis of Apidpic Acid," Biotechnology Progress, American Institute of Chemical Engineers. 18(2): 201-211 (2002).
International Search Report for International Application No. PCT/US2012/032774 mailed on Jul. 19, 2012.
Hizuka et al., Preparation of 2,6-Dioxabicyclo [3.3.0]octan-3,7-dione and Its Application to the Synthesis of (±)—Eldanolide. Chem. Pharm. Bull. 36:1550-1553 (1988).
International Preliminary Report on Patentability for International Application No. PCT/US2012/032741 mailed on Oct. 24, 2013.
International Preliminary Report on Patentability for International Application No. PCT/US12/32774 mailed on Oct. 24, 2013.

*Primary Examiner* — Noble Jarrell
(74) *Attorney, Agent, or Firm* — Greenberg Traurig, LLP; Fang Xie

(57) ABSTRACT

Provided herein are processes for preparing caprolactam from a starting material such as one or more of the cis,cis-, cis,trans- and trans,trans-double-bond isomers of muconamide, muconic acid ester, or muconic acid. The starting material, intermediates, and caprolactam prepared therefrom can contain carbon atoms derived from biomass containing detectable $^{14}$C content determined according to ASTM D6866 and optionally containing a $^{14}$C content up to 0.0000000001% (one part per trillion). Caprolactam so prepared can be used to make various polyamides.

58 Claims, No Drawings

PROCESS FOR PREPARING CAPROLACTAM AND POLYAMIDES THEREFROM

CROSS REFERENCE TO RELATED APPLICATION

This application claims priority to and the benefit of U.S. Provisional Application No. 61/473,754, filed Apr. 9, 2011, U.S. Provisional Application No. 61/473,753, filed Apr. 9, 2011, and PCT International Patent Application entitled "Process for Preparing Hexamethylenediamine and Polyamides Therefrom", Attorney Docket No. 136556-013002/PCT filed in the United States Receiving Office on Apr. 9, 2012, each of which is incorporated herein by reference in its entirety.

FIELD OF THE INVENTION

The present invention provides improved processes for the preparation of caprolactam from a starting material such as one or more of the cis,cis-, cis,trans- and trans,trans-double-bond isomers of muconamide, muconic acid ester, or muconic acid. Novel intermediates made in these processes are also provided. The described processes also enable caprolactam to be made from carbon atoms derived from renewable biomass.

BACKGROUND OF THE INVENTION

Caprolactam is an important industrial chemical that is used widely for manufacturing of polymeric material such as nylon 6. Certain industrial processes for making caprolactam are well known in the patent literature. Conventionally, caprolactam is made by first converting materials derived from petrochemical feedstock such as cyclohexane, phenol or toluene, to cyclohexanone 2, treating with hydroxylamine to produce the corresponding oxime 3 followed by an acid-induced Beckmann Rearrangement to give caprolactam 1 as shown in Scheme 1. Such a process is described in, for example, U.S. Pat. Nos. 3,914,217; 5,264,571; 4,804,754; 5,354,859 and 7,351,820.

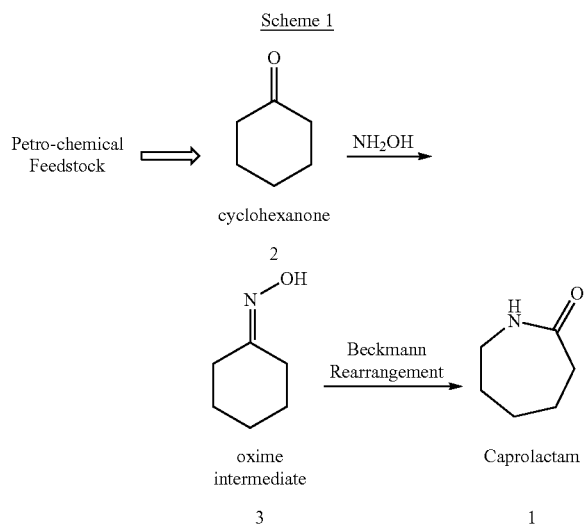

A disadvantage of this existing technology is that large amounts of ammonium sulfate—up to 4.5 tonnes per tonne of caprolactam are produced. Much development work is concentrating on reducing or even eliminating this sulfate by-product. For example, DSM's Hydroxylamine Phosphate Oxime (HPO)-plus process has substantially reduced this sulfate by-product to 1.5 tonnes/tonne of caprolactam. [Chem. Week, 2000, 162(32), 17; Dahlhoff, G., et al., Catal. Revs., 2001, 43(4), 389; "Encyclopedic dictionary of named processes in chemical technology", Alan E. Comyns, CRC Press, 2007, p. 172.

A more recent approach, developed by EniChem and commercialized by Sumitomo in 2003, completely eliminates the production of ammonium sulfate. The chemical reaction in this case is a so-called ammoximation reaction, whereby cyclohexane is reacted with ammonia and hydrogen peroxide at around 90° C. in the presence of a titanium silicate-2 catalyst [Reddy, J. S., et al., P., J. Mol. Catal., 1991, 69, 383. Chem. Br., 1995, 31(2), 94]. This process allows for considerable cost savings since no hydroxylamine plant is needed. However, hydrogen peroxide is expensive and must be manufactured on a large scale to provide sensible scale economies and transfer pricing.

Another improvement of this process developed by Toray Industries of Japan utilizes a photochemical process for making caprolactam from cyclohexane in the presence of nitrosyl chloride and hydrogen chloride, without the use of the oximation step. This process provides substantial capital cost savings, with the elimination of both cyclohexanone, hydroxylamine and oximation plants. However, the process requires access to low-cost power to be truly cost effective. Large scale photochemical reactors are difficult to design and require constant cleaning to remove tar-like reaction residues. [Hydrocarbon Process. Int. Ed., 1989, 68(11), 97; Dahlhoff, G., et al., Catal. Revs., 2001, 43(4), 389.]

Other notable processes developed by DSM, Shell, BASF, DuPont and Rhodia use butadiene or adiponitrile as starting material for manufacturing caprolactam. Altam, a process developed by DSM and Shell, uses butadiene and carbon monoxide feedstocks to make caprolactam without ammonium sulfate production. The process employs four steps—carbonylation, hydroformylation, reductive amination and cyclization and DSM claims has allowed cost reductions of 25-30% through simplification of plant operations and lower energy consumption.

BASF, Rhodia, and DuPont also investigated the feasibility of converting butadiene to caprolactam. Both BASF and Rhodia' processes involve the hydrogenation of adiponitrile, which can be manufactured from butadiene and hydrogen cyanide, or by electrolysis from acrylonitrile to make 6-aminocapronitrile with hexamethylenediamine as a co-product, using different operating conditions and catalysts.

Other processes for making of caprolactam are also available in the literature using starting materials other than those already mentioned. For instance, U.S. Pat. No. 2,351,939 describes a vapor phase synthesis of caprolactam from adipic acid, using a Ni catalyst in the presence of $H_2$ and $NH_3$, with dehydrating agents (boric and phosphoric acids). The process provided 45% of caprolactam along with 18% of HMI formed. Another synthesis of caprolactam from adipic acid is described in U.S. Publication No. US2007/0244317 where a homogeneous ruthenium catalyst was used leading to a series of products formed, including the dimethyl adipamide and 8% of caprolactam.

U.S. Pat. No. 4,800,227 describes the use of two catalysts (Pd+Ru, Rh or Re) to produce lactams from $C_4$-$C_6$ dicarboxylic acids.

Another process using dicarboxylic acids was described in U.S. Pat. Nos. 4,263,175 and 4,356,124 where Ru oxide or an oxide complex of Ru, Fe, Ni, Co was used to make pyrrolidone. Still another process based on the hydrogenation of dicarboxylic acids with Ru or Os in the presence of an organic phosphine is described in U.S. Publication No. US2007/0244317, which uses N-methylamine to produce N-methyl caprolactam from adipic acid. A number of other products are observed, including some caprolactam.

However, the above mentioned processes all involve using petroleum-derived chemicals or petrochemicals as a starting material. Because of the reliance of these processes on non-renewable petroleum, there is an urgent need to find processes for making chemicals from renewable sources such as biomass, as a way to reduce mankind's dependence on crude oil, to increase the use of renewable energy sources, and to reduce air and water pollution from the petrochemical industry.

Clearly, it would be advantageous to have an alternative and improved process for making caprolactam from a renewable biomass source, while providing higher yield and generating fewer by-products.

BRIEF SUMMARY OF THE INVENTION

The present invention, in one aspect, provides novel processes using carbon atoms derived from renewable biomass to produce caprolactam. The renewable biomass can contain detectable $^{14}C$ content determined according to ASTM D6866, and optionally can contain a $^{14}C$ content up to 0.0000000001% (one part per trillion). Specifically, one aspect of the present invention relates to a process for preparing caprolactam 1 of the formula:

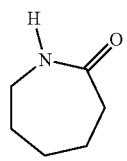

1 which process includes reacting one or more of cis,cis-, cis,trans- and trans,trans-muconic acid (Q,Q-MA, 3a-3c), structures shown below in Structure Scheme 2, with ammonia and hydrogen, in the presence of a catalyst; and forming caprolactam 1 therefrom.

In certain embodiments, the one or more of Q,Q-MA 3a-3c can be directly converted to caprolactam 1 under suitable conditions such as solvent, pressure, temperature, and catalyst.

In some embodiments, one or both of the cis,cis- or cis,trans-muconic acid (Q,Q-MA 3a, 3b) can be first converted to an intermediate, $\Delta^\alpha$-muconolactone and/or $\Delta^\beta$-muconolactone 5, structures also shown in Structure Scheme 2, which are then reacted in the presence of ammonia, hydrogen and a catalyst under suitable conditions such as temperature and pressure such that caprolactam 1 is formed.

In some embodiments, the one or more of Q,Q-MA 3a-3c (structures shown in Structure Scheme 2) can be first converted to one or more of cis,cis-, cis,trans- and trans,trans-muconate diester. In some variations, the muconate diester is one or more of cis,cis-, cis,trans- and trans,trans-dimethyl muconate (Q,Q-DMM, 6a-6c), with structures shown in Structure Scheme 2. The muconate diester (e.g., Q,Q-DMM 6a-6c) can then be converted to one or more of cis,cis-, cis,trans- and trans,trans-muconamide (Q,Q-MCA, 4a-4c), structures also shown below in Structure Scheme 2. The Q,Q-MCA 4a-4c can then be reacted in the presence of ammonia, hydrogen and a catalyst under conditions such as temperature and pressure such that caprolactam 1 is formed. It should be noted that adipamide 7 may be formed as an intermediate in the preparation of caprolactam 1 from muconamide (Q,Q-MCA, 4a-4-c).

In further embodiments, one or more of Q,Q-MA 3a-3c can be converted to muconate diester (e.g, Q,Q-DMM 6a-6c), which is then converted to Q,Q-MCA 4a-4-c. The Q,Q-MCA 4a-4-c can then be hydrogenated with hydrogen under suitable conditions such as pressure, temperature and catalyst to form adipamide 7, structure also shown below in Structure Scheme 2. The adipamide 7 can then be further reacted in the presence of ammonia, hydrogen and a catalyst under conditions such as temperature and pressure such that caprolactam 1 is formed.

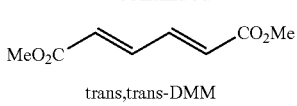

trans,trans-DMM cis,cis-, cis,trans-, and trans,trans- double-bond isomers of DMM 6a-6c (Q,Q-DMM)

The present invention, in another aspect, provides a process for the preparation of caprolactam 1 from muconic acid Q,Q-MA obtained from various sources. The process includes reacting one or more of cis, cis-, cis,trans- and trans, trans-muconic acid (Q,Q-MA), with ammonia and hydrogen, in the presence of a catalyst; and forming caprolactam 1 therefrom. The reacting step can include reactions via any of the following routes, or combinations, variations and modifications thereof.

Route 1 (1 step) includes: converting Q,Q-MA to caprolactam 1 in an aprotic polar solvent, using $H_2$ and $NH_3$ gases, and in the presence of at least one catalyst. In some embodiments, the total initial pressure of the $H_2$ and $NH_3$ gases in Route 1 is about 250 to about 2050 psi, and the temperature is about 200 to about 300° C.

In certain embodiments of Route 1, the aprotic polar solvent can be 1,4-dioxane, diglyme or DMSO. Optionally, the aprotic polar solvent can be mixed with water or an alcohol. In some examples, the alcohol is MeOH. The at least one catalyst in Route 1 can be or can comprise one or more of Pd, Pt, Rh and Ru. In some embodiments, the at least one catalyst is or comprises two or more metals, e.g., Ru and Pt or Ru and Pd. The at least one catalyst may be present at from about 0.3 to about 1 mol %. In various embodiments, the converting step in Route 1 takes about 0.5 to about 3 hours.

Route 2 (2 steps) includes: (1) converting one or both of the cis,cis-MA and cis,trans-MA to one or both of $\Delta^\alpha$-muconolactone and $\Delta^\beta$-muconolactone; and (2) reacting one or both of $\Delta^\alpha$-muconolactone and $\Delta^\beta$-muconolactone to form caprolactam 1, using $H_2$ and $NH_3$ gases, and in the presence of at least one catalyst.

In some variations, step (1) of Route 1 is conducted by heating the MA at reflux in aq. acetic acid. In certain embodiments, in Route 2, step (1) the aq. acetic acid is mixed with water at a ratio of about 1:2 acetic acid:water.

In some embodiments, step (2) of Route 2 is conducted with $H_2$ and $NH_3$ gases at a total initial pressure from about 250 to about 650 psi, and at a temperature from about 200 to about 300° C. In Route 2, step (2) the at least one catalyst can be or can comprise one or more of Pd, Pt, Rh and Ru. In some variations, the at least one catalyst is or comprises two or more of Pd, Pt, Rh and Ru. For example, in Route 2, step (2) the at least one catalyst can be or comprise Ru and Pd. The at least one catalyst is present at from about 0.5 to about 5 mol %. In some examples, Route 2, step (2) takes about 0.5 to about 3 hours.

Route 3 (3 steps) includes: (1) converting Q,Q-MA to one or more of cis,cis-, cis,trans- and trans,trans-muconate diester (e.g., Q,Q-DMM); (2) converting the muconate diester (e.g., Q,Q-DMM) to one or more of cis,cis-, cis,trans- and trans, trans-muconamide (Q,Q-MCA) in aq. $NH_3$; and (3) converting Q,Q-MCA to caprolactam 1 in an aprotic polar solvent, using $H_2$ and $NH_3$, and in the presence of a catalyst.

In step (1) of Route 3, Q,Q-MA can be converted to the muconate diester using any suitable method. In some cases, Q,Q-MA is converted to one or more of cis,cis-, cis,trans-, and trans,trans-muconate diester (e.g., Q,Q-DMM) in aq. NaOH with dimethyl sulfate, e.g., at room temperature. In some variations, trans,trans-MA is converted to trans,trans muconate diester (e.g., trans,trans-DMM) in methanol containing a catalytic amount of sulfuric acid while heating at reflux.

In Route 3, step (2), the aq. $NH_3$ can be mixed with an alcohol in some variations. In some non-limiting examples, the alcohol is MeOH or EtOH. A ratio of the aq. $NH_3$ to the alcohol may be about 1:1.

In Route 3, step (3) the aprotic polar solvent can be THF, 1,4-dioxane or diglyme. In some embodiments, the catalyst in Route 3, step (3) is or comprises 2CuO—$Cr_2O_3$ or Pd. The catalyst may be present at from about 5 to about 50 mol %. In some variations, step (3) of Route 3 is conducted using a total initial pressure of $H_2$ and $NH_3$ from about 1000 to about 1600 psi, and a temperature from about 200 to about 300° C. In some examples, Route 3, step (3) takes about 1 to about 3 hours.

Route 4 (4 steps) includes: (1) converting Q,Q-MA to one or more of cis,cis-, cis,trans- and trans,trans-muconate diester (e.g., Q,Q-DMM); (2) converting cis,cis-, cis,trans- or trans, trans-muconate diester (e.g., Q,Q-DMM) to one or more of cis,cis-, cis,trans- and trans,trans-muconamide (Q,Q-MCA) in aq. $NH_3$; (3) reducing the Q,Q-MCA to adipamide using $H_2$, in the presence of a first catalyst; and (4) reducing the adipamide to yield caprolactam 1 in an aprotic polar solvent, using $H_2$ and $NH_3$ gases, in the presence of a second catalyst.

In step (1) of Route 4, Q,Q-MA can be converted to the muconate diester using any suitable method. In some cases, Q,Q-MA is converted to one or more of cis,cis-, cis,trans-, and trans,trans-muconate diester (e.g., Q,Q-DMM) in aq. NaOH with dimethyl sulfate, e.g., at room temperature. In some variations, trans,trans-MA is converted to trans,trans muconate diester (e.g., trans,trans-DMM) in methanol containing a catalytic amount of sulfuric acid while heating at reflux.

In Route 4, step (2), the aq. $NH_3$ can be mixed with an alcohol in some variations. In some non-limiting examples, the alcohol is MeOH or EtOH. A ratio of the aq. $NH_3$ to the alcohol may be about 1:1.

In some variations, Route 4 step (3) is conducted at an initial pressure from about 300 to about 1600 psi, and a temperature from about 200 to about 300° C. In some embodiments, in Route 4, step (3) the first catalyst can be or comprise 2CuO—$Cr_2O_3$, Pd, Pt, Rh or Ru. The first catalyst can be present from about 5 to about 25 mol %.

In Route 4, step (4) the aprotic polar solvent can be diglyme. In some embodiments, the second catalyst in Route 4, step (4) can be or can comprise Pd, Pt, Rh or Ru. The second catalyst can be present from about 5 to about 10 mol %. In some embodiments, Route 4 step (4) is conducted at a total initial pressure from about 500 to about 1650 psi, and a temperature from about 200 to 300° C. In some examples, Route 4, step (4) takes about 1 to about 3 hours.

Route 5 (2 steps) includes: (1) converting one or more of cis,cis-, cis,trans- and trans,trans-muconic acid (Q,Q-MA) to adipic acid 10 using hydrogen and a catalyst, and (2) catalytically reducing adipic acid 10 to caprolactam 1, using $H_2$ and $NH_3$ gases, and in the presence of at least one catalyst. In some cases, Route 5 step (2) is carried out in an aprotic polar solvent. In some cases in Route 5 step (2), the initial ammonia pressure is about 50-60 psi, the initial hydrogen pressure is about 600-1500 psi, the reaction temperature is 250° C., the reaction time is 2 hours (including time to ramp up from room temperature).

Another aspect of the present invention relates to compounds and intermediates prepared according to the methods and processes disclosed herein. In particular, such compounds and intermediates can contain detectable $^{14}C$ content determined according to ASTM D6866. In various embodiments, the compounds and intermediates can contain up to 0.0000000001% $^{14}C$.

A further aspect of the present invention relates to a process for preparing nylon 6. The process includes polymerizing caprolactam, which is prepared from a biomass-derived muconic acid and contains a detectable amount of $^{14}C$ determined according to ASTM D6866. In some embodiments, the process can also include: reacting one or more of cis, cis-, cis,trans- and trans,trans-muconic acid (Q,Q-MA), with ammonia and hydrogen, in the presence of a catalyst; and forming caprolactam therefrom. In some examples, the caprolactam contains up to 0.0000000001% $^{14}C$. Nylon 6 prepared according to any of these processed is also included in the present invention. In some embodiments, the nylon 6 contains a detectable amount of $^{14}C$ determined according to ASTM D6866, e.g., up to 0.0000000001% $^{14}C$.

Another aspect of the present invention relates to a process for preparing polyamides and copolymers thereof. The process includes reacting caprolactam with a compound having at least two amide-forming groups, wherein the caprolactam is prepared from a biomass-derived muconic acid and contains a detectable amount of $^{14}C$ determined according to ASTM D6866. In some embodiments, the process can also include: reacting one or more of cis, cis-, cis,trans- and trans, trans-muconic acid (Q,Q-MA), with ammonia and hydrogen, in the presence of a catalyst; and forming caprolactam therefrom. In some examples, the caprolactam contains up to 0.0000000001% $^{14}C$. In certain embodiments, the compound having at least two amide-forming groups comprises one or more of aliphatic or aromatic amino carboxylic acids, aliphatic or aromatic diamines, aliphatic or aromatic dicarboxylic acids, or salts or halides or esters thereof. Polyamides and copolymers thereof prepared according to any of these processed are also included in the present invention. In some embodiments, the polyamide contains a detectable amount of $^{14}C$ determined according to ASTM D6866, e.g., up to 0.0000000001% $^{14}C$.

ABBREVIATIONS AND DEFINITIONS

Unless defined otherwise, all technical and scientific terms used herein have the same meaning as commonly understood by one of ordinary skill in the art to which this invention belongs. Reference is made here to a number of terms that shall be defined to have the following meanings.

"acac" means acetylacetonate.

AcOH means acetic acid.

"Alcohol" as used herein means an alcohol that comprises a $C_{1-20}$ alkyl moiety substituted at one, two or more hydrogen atoms with one, two or more hydroxyl groups. Alcohols include methanol, ethanol, n-propanol, i-propanol, n-butanol, i-butanol, s-butanol, t-butanol, n-pentanol, i-pentanol, n-hexanol, cyclohexanol, n-heptanol, n-octanol, n-nonanol, n-decanol, ethylene glycol and glycerol. The carbon atoms in alcohols can be straight, branched or cyclic. Alcohol includes any subset of the foregoing, e.g., $C_{1-6}$ alcohols (alcohols having 1, 2, 3, 4, 5 or 6 carbon atoms).

"Alkyl" refers to a group having the general formula $C_nH_{2n+1}$ derived from a saturated, straight chain or branched aliphatic hydrocarbon, where n is an integer. In certain embodiments, n is from 1 to about 30, from 1 to about 20, or from 1 to about 10. Non-limiting examples of alkyl groups include $C_1$-$C_8$ alkyl groups such as methyl, ethyl, propyl, isopropyl, 2-methylpropyl, 2-methylbutyl, 3-methylbutyl, 2,2,-dimethylpropyl, 2-methylpentyl, 3-methylpentyl, 4-methylpentyl, 2-2-dimethylbutyl, 3,3-dimethylbutyl, 2-ethylbutyl, n-butyl, isobutyl, tert-butyl, isopentyl, n-pentyl, neopentyl, n-hexyl, isohexyl, n-heptyl, isoheptyl, n-octyl, isooctyl, n-nonyl, isononyl, n-decyl and isodecyl. An alkyl group may be unsubstituted, or may be substituted. In some embodiments, the alkyl group is straight chain having 1, 2, 3, 4, 5, 6, 7, 8, 9, 10, 11 or 12 carbons. In some embodiments, the alkyl group is branched having 1, 2, 3, 4, 5, 6, 7, 8, 9, 10, 11 or 12 carbons. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

"aq." means aqueous.

"Aryl" refers to an organic radical derived from a monocyclic or polycyclic aromatic hydrocarbon by removing a hydrogen atom. Non-limiting examples of the aryl group include phenyl, naphthyl, benzyl, or tolanyl group, sexiphenylene, phenanthrenyl, anthracenyl, coronenyl, and tolanylphenyl. An aryl group can be unsubstituted or substituted with one or more suitable substituents. Furthermore, the aryl group can be monocyclic or polycyclic. In some embodiments, the aryl group contains at least 6, 7, 8, 9, or 10 carbon atoms. Non-limiting examples of moieties with which the aryl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The ASTM D6866 specifications, "Standard Test Methods for Determining the Biobased Content of Solid, Liquid, and Gaseous Samples Using Radiocarbon Analysis" as published by ASTM International, are incorporated herein by reference in its entirety.

Biomass refers to the carbon atoms in the form of cellulose, lignocellulose, hemicellulose, starch and other carbohydrate polymers contained in nonfood and food plants, for example but not limited to, corn, sweet sorghum and sugar cane, and the waste materials produced from growing or processing them which cannot be used as a food source, but which can be broken down to simple sugars which can be converted into cis,cis-muconic acid and other compounds described herein. Such compounds contain detectable $^{14}C$ content determined according to ASTM D6866 and optionally contain a $^{14}C$ content up to 0.0000000001% (one part per trillion).

A catalyst support refers to a material, usually a solid with a high surface area, to which a catalyst is affixed. The support may be inert or participate in the catalytic reactions. Examples of suitable supports include various forms of carbon (e.g., charcoal), alumina (e.g., $Al_2O_3$) and silica (e.g., Davisil® 635). Any catalysts described herein, or combinations thereof, can be provided on a catalyst support.

DMM means dimethyl muconate.

DMSO means dimethyl sulfoxide.

EtOH means ethanol.

"g" means gram(s).

GC means gas chromatography.

GCMS means gas chromatography mass spectroscopy.

HMDA means hexamethylenediamine.

HMI means hexamethyleneimine.
HPLC means high pressure liquid chromatography.
hr means hour(s).
iPrOH means isopropanol.
L means liter.
MA means muconic acid.
MCA means muconamide.
MeOH means methanol.
min means minute(s).
mL means milliliter.
"mol" means the mole unit. "mol %" in the context of catalyst amount, means the molar percentage of the actual metal of a given catalyst relative to the moles of reactant.
"m.p." means melting point.
NMR means nuclear magnetic resonance.

The term "optional" or "optionally" means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where the event or circumstance does not occur.

$PPh_3$ means triphenylphosphine.

Q,Q-DMM means one or more of cis,cis-, cis,trans-, or trans,trans-double-bond isomers of dimethyl muconate. It should be understood that in the synthesis routes provided herein, dimethyl muconate can be replaced by any other muconate diester as described herein.

Q,Q-MA means one or more of cis,cis-, cis,trans-, or trans,trans-double-bond isomers of muconic acid.

Q,Q-MCA means one or more of cis,cis-, cis,trans-, or trans,trans-double-bond isomers of muconamide.

RT means ambient temperature or room temperature, from about 20° C. to about 25° C.

Unless otherwise noted, a "solvent" used herein refers to organic solvents. Organic solvents include protic polar solvents, aprotic polar solvents, and non-polar solvents. Non-limiting examples of protic polar solvents include methanol, ethanol, n-butanol, isopropanol, n-propanol, acetic acid, formic acid, hydrogen fluoride, and ammonia. Non-limiting examples of aprotic polar solvents include dimethylformamide, dimethylsulfoxide (DMSO), methoxymethyl ether, ethyl ether, diethyl ether, tert-butyl methyl ether (TBME), diglyme (bis(2-methoxyethyl) ether), tetraglyme (tetraethylene glycol dimethyl ether), cyclopentyl methyl ether, ethyl acetate, tetrahydrofuran (THF), methyl THF, dioxane, acetone, acetonitrile and propionitrile. Non-limiting examples of non-polar organic solvents include benzene, toluene, pentane, hexane, cyclohexane, heptane, octane, nonane and decane. A mixture of two or more of any of these can be used.

"Substituted" as used to describe a compound or chemical moiety refers to where at least one hydrogen atom of that compound or chemical moiety is replaced with a second chemical moiety. The second chemical moiety can be any desired substituent that does not adversely affect the desired activity of the compound. Examples of substituents are those found in the exemplary compounds and embodiments disclosed herein, as well as halogen; alkyl; heteroalkyl; alkenyl; alkynyl; aryl, heteroaryl, hydroxyl; alkoxyl; amino; nitro; thiol; thioether; imine; cyano; amido; phosphonato; phosphine; carboxyl; thiocarbonyl; sulfonyl; sulfonamide; acyl; formyl; acyloxy; alkoxycarbonyl; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —$CO_2CH_3$; —$CONH_2$; —$OCH_2CONH_2$; —$NH_2$; —$SO2NH_2$; —$OCHF_2$; —$CF_3$; —$OCF_3$; —NH(alkyl); —N(alkyl)$_2$; —NH(aryl); —N(alkyl)(aryl); —N(aryl)$_2$; —CHO; —CO(alkyl); —CO(aryl); —$CO_2$(alkyl); and —$CO_2$(aryl); and such moieties can also be optionally substituted by a fused-ring structure or bridge, for example —$OCH_2O$—. These substituents can optionally be further substituted with a substituent selected from such groups. All chemical groups disclosed herein can be substituted, unless it is specified otherwise.

TBME means t-butyl methyl ether.
THF means tetrahydrofuran.
TLC means thin-layer chromatography.
Tonne(s) means metric ton(s).
TRIPHOS means 1,1,1-tris(diphenylphosphinomethyl)ethane.
"wt %" means weight percent.

In the following description, all numbers disclosed herein are approximate values, regardless whether the word "about" or "approximate" is used in connection therewith. They may vary by 1 percent, 2 percent, 5 percent, or, sometimes, 10 to 20 percent. Whenever a numerical range with a lower limit, $R^L$, and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

DETAILED DESCRIPTION

It is understood that the terminology used herein is for the purpose of describing particular embodiments only and is not intended to be limiting. As used in this specification, the singular forms "a", "an", and "the" include plural referents unless the content clearly indicates otherwise.

Also, certain patents and published applications have been incorporated by reference. However, the text of such patents is only incorporated by reference to the extent that no conflict exists between such text and other statements set forth herein. In the event of such conflict, then any such conflicting text in such incorporated by reference patent or application is specifically not so incorporated herein.

The conversion of biomass to cis,cis-muconic acid can be found in U.S. Pat. Nos. 4,879,987 and 5,487,987, both of which patents are incorporated herein by reference in their entirety. The biomass-derived cis,cis-, cis,trans-, and trans,trans-muconic acid materials may be converted to the various double-bond isomers of Q,Q-DMM according the methods described in WO 2010/148063, WO 2010/148080, WO 2010/148049, WO 2010/148081 and WO 2010/148070, all of which applications are incorporated herein by reference in their entirety.

Caprolactam

In contrast to the known processes, the present invention, in certain embodiments, provides a new approach for the synthesis of caprolactam 1 from a renewable starting material obtained from biomass. The renewable starting material can be one or more of the double-bond isomers of the Q,Q-MA. In some embodiments, any or both of the double-bond isomers of Q,Q-MA 3b-3c can be prepared from cis,cis-muconic acid (cis,cis-MA 3a). Cis,cis-MA can be produced, for example, via fermentation of sugars derived from biomass which can contain detectable $^{14}C$ content determined according to ASTM D6866. In some embodiments, the biomass can contain a $^{14}C$ content up to 0.0000000001% (one part per trillion). The biomass-derived cis,cis-MA 3a can be converted to the cis,trans- and trans,trans-double-bond isomers of muconic acid (Q,Q-MA 3b, 3c), and then to the double-bond isomers of muconolactone 5 (see Starting Materials, Example I). The various double-bond isomers of muconic acid can be converted to various isomers of dimethyl muconate (Q,Q-DMM, 6a-6c) and then to isomers of muconamide (Q,Q-MCA 4a-4-c) according the methods described below (see Starting Materials, Examples A through H). Thus, all of the double-bond isomers of all starting materials and intermediates may be derived from biomass and not derived from petrochemical feedstock. Such starting material derived from biomass has not been previously available.

It should be noted that when any of the double-bond isomers (e.g., cis,cis-) is converted to another double-bond isomer (e.g., cis,trans-) in a process of the present invention, the conversion may provide predominantly the isomer indicated, although it is understood that some of the other isomer(s) can be present.

Various routes to make caprolactam 1 are provided by the present invention, where each can have different advantages. In some situations, routes utilizing the trans-trans-isomer of the intermediates may be preferred. Further, the routes with fewer steps can also be preferred in some instances. However, the multiplicity of routes available in the present invention allows specific routes to be chosen based on, for example, various practical factors, such as availability of pressure equipment, the higher yield and/or fewer by-products, which may make a given route more advantageous than other routes.

Certain embodiments of the present invention for the production of caprolactam 1 are illustrated by Scheme 3 (Routes 1-4) and Schemes 4A and 4B (Route 5) below. Scheme 4B illustrates various intermediates that may be formed in the one pot synthesis of adipic acid to caprolactam illustrated in Scheme 4A. It should be noted that any suitable diester of MA can be used in place of DMM in reactions illustrated in Scheme 3. In some cases, DMM is used, e.g., because DMM may be less expensive or cheaper to make from MA than other diesters of MA. The MA diester has formula $R^1OOC-C=C-C=C-COOR^2$, where $R^1$ and $R^2$ can be the same or different, and $R^1$ and $R^2$ are each individually any alkyl, alkenyl, alkynyl, aryl, cyclalkyl, cycloalkenyl, alkaryl and aralkyl group that is unsubstituted or substituted.

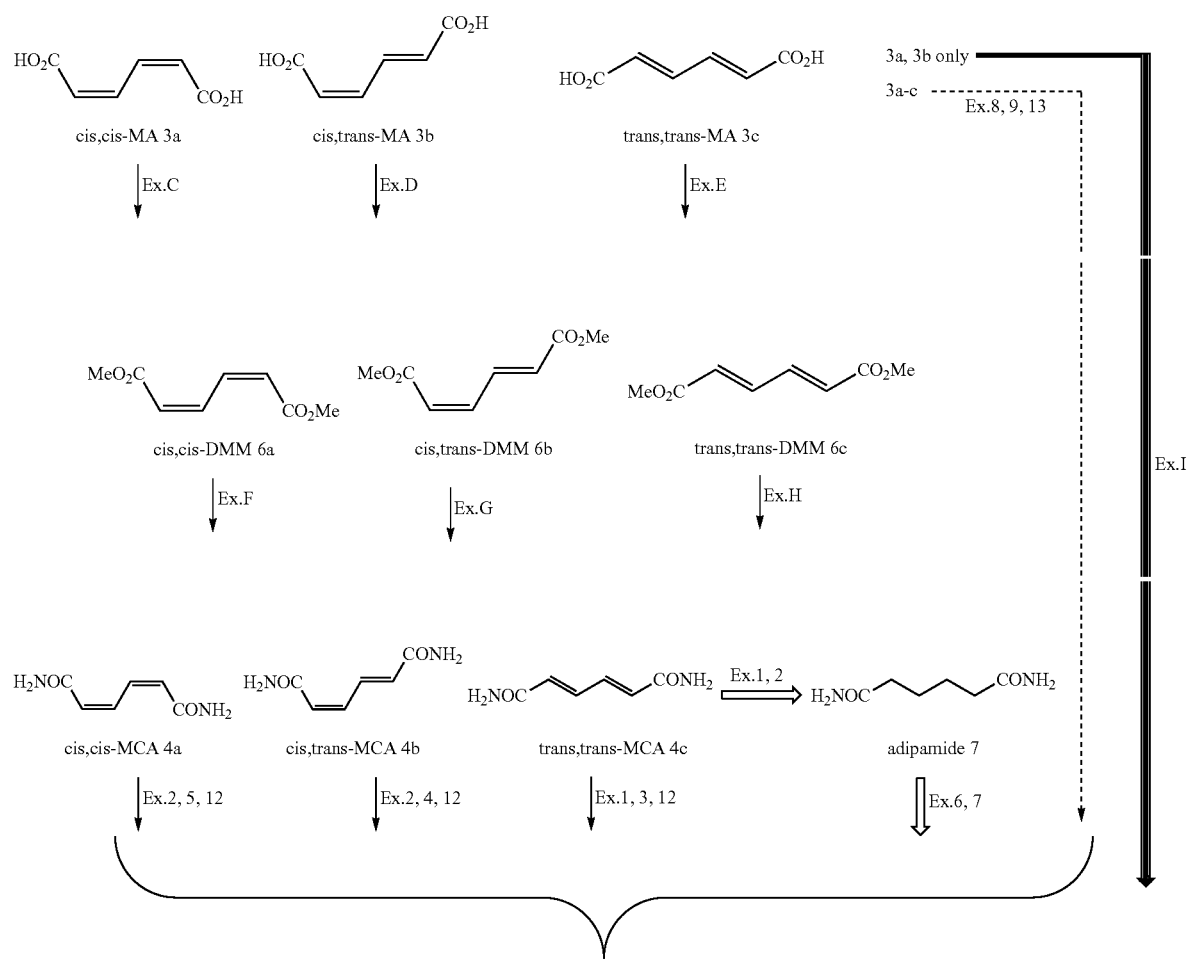

Scheme 3 (Route and Example Numbers for each step are indicated)

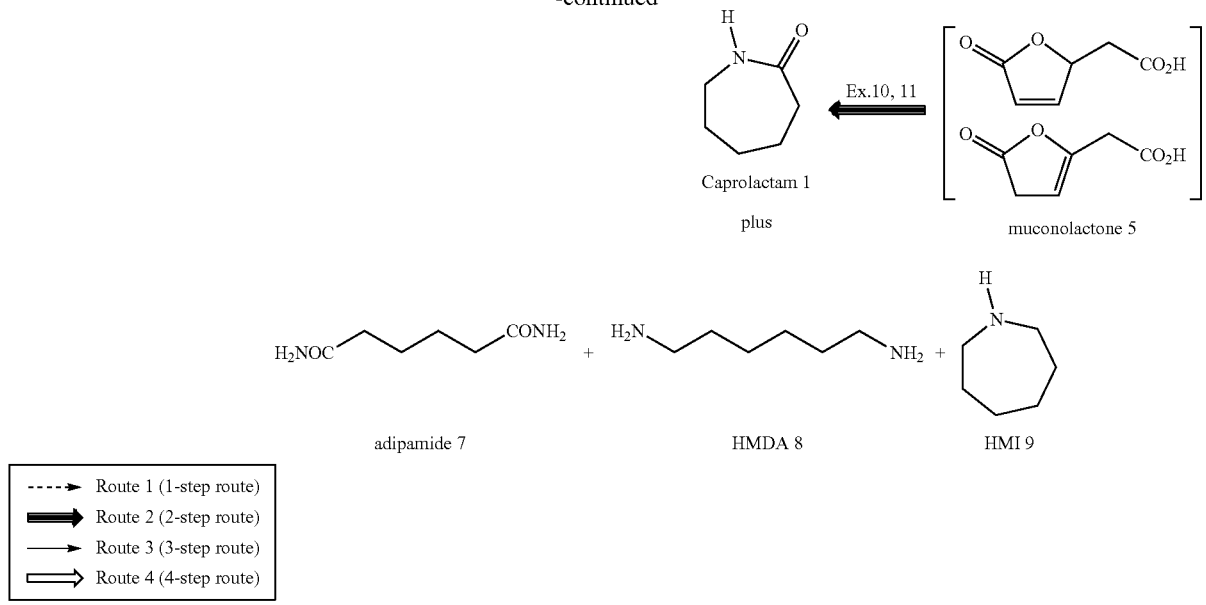
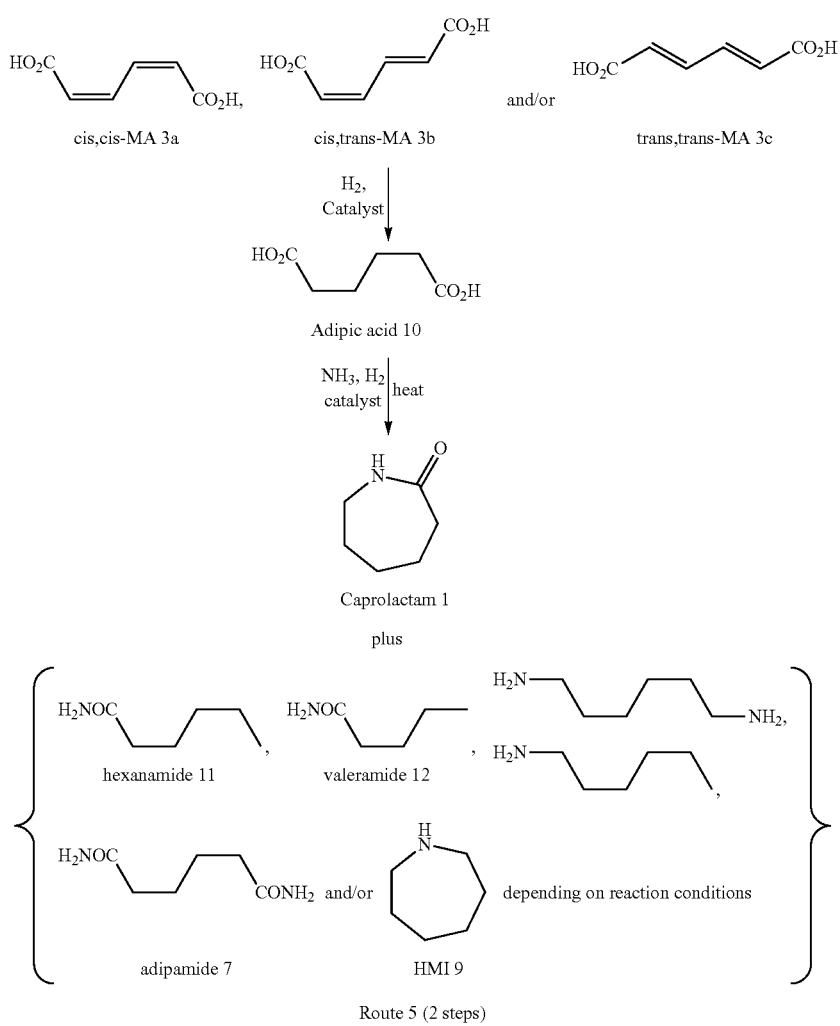

Scheme 4B

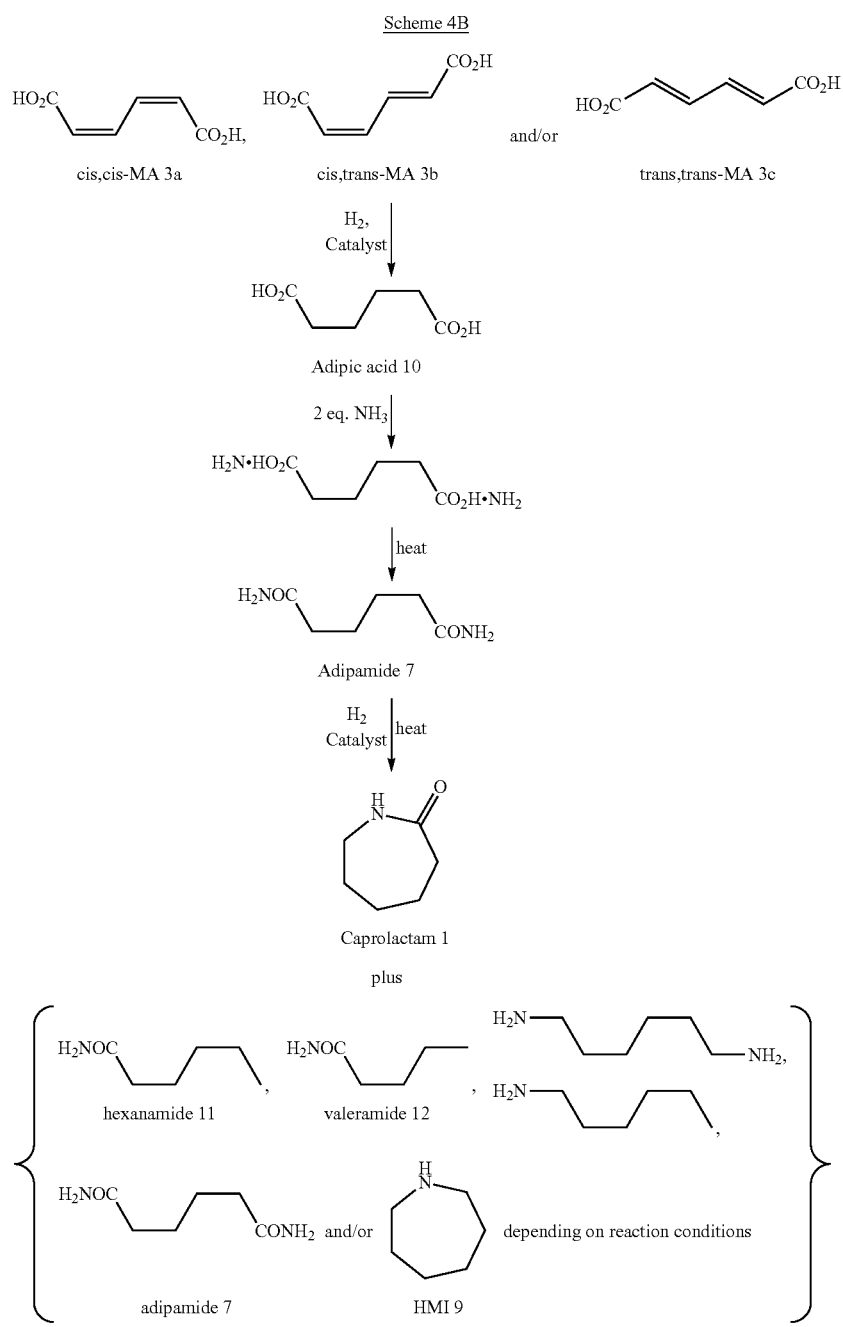

As illustrated in Schemes 4A-4B, Route 5 includes: (1) converting one or more of cis,cis-, cis,trans- and trans,trans-muconic acid (Q,Q-MA) to adipic acid 10 using hydrogen and a catalyst, and (2) catalytically reducing adipic acid 10 to caprolactam 1, using $H_2$ and $NH_3$ gases, and in the presence of at least one catalyst. In some cases, Route 5 step (2) is carried out in an aprotic polar solvent.

Route 5 step (1) is accomplished using any known hydrogenation conditions for converting muconic acid to adipic acid. In some cases, a catalyst comprising Pd or Pt is used. In some cases, a Ni catalyst (e.g., Ni/$Al_2O_3$ or Ni/$Al_2O_3$—$SiO_2$) is used. In some cases, the hydrogenation is carried out in a batch reactor, and in other cases, the hydrogenation is carried out in a flow reactor. In some cases, the hydrogenation is carried out in THF using a Ni catalyst.

Route 5 step (2) is carried out using reaction conditions (catalyst, temperature, ammonia pressure, hydrogen pressure, solvent) sufficient to amidate the adipic acid to make adipamide 7 and the catalytic reduction continues to form caprolactam 1. An excess of ammonia is present. In some cases, an excess of ammonia of about 1.0 equivalents is used. In some embodiments, the initial ammonia pressure is about 50-60 psi. In some embodiments, the initial hydrogen pressure is about 200-2000 psi. In some embodiments, the total initial pressure of the $H_2$ and $NH_3$ gases in Route 5 step (2) is about 250 to about 2050 psi, and the temperature is about 200 to about 300° C.

In Route 5 step (2), the aprotic polar solvent can be any suitable solvent. In some cases, the solvent is 1,4-dioxane, diglyme, DMSO, cyclopentyl methyl ether, dibutyl ether, or diethoxyethane. In some cases, the solvent is tetrahydrofuran (THF). Optionally, the aprotic polar solvent may be mixed with water or an alcohol. In some examples, the alcohol is MeOH.

The at least one catalyst in Route 5 step (2) can be or can comprise one or more of Pd, Pt, Rh and Ru. In some embodiments, the at least one catalyst is or comprises two or more metals, e.g., Ru and Pt or Ru and Pd. In some cases, the catalyst is $Ru/Al_2O_3$, e.g., 5% $Ru/Al_2O_3$. The at least one catalyst may be present at a catalyst loading from about 0.01 mol % to about 1 mol %, about 0.05 mol % to about 1 mol %, about 0.1 mol % to about 1 mol %, or about 0.3 mol % to about 1 mol %.

In some embodiments, in Route 5 step (2) ammonia gas is first introduced to the reactor at room temperature. Introduction of ammonia gas causes formation of a diammonium salt via an exothermic reaction. After the ammonia pressure has stabilized at 50-60 psi, hydrogen is introduced into the reactor so that the total pressure is about 250-2050 psi and the reactor is heated to the reaction temperature of 200-300° C. In some cases, the reactor is heated before hydrogen is introduced. As shown in Schemes 4A-4B, adipamide 7 is initially formed from the diammonium salt, and as the reaction progresses, adipamide 7 is converted to caprolactam 1.

The time and temperature of Route 5 step (2) are optimized to form the desired caprolactam but to avoid formation of HMI 9, valeramide 11, or hexaneamide 12. The temperature is at least high enough to reduce adipamide 7, e.g., at least 180-200° C. In various embodiments, Route 5 step (2) takes about 0.5 to about 3 hours. In some variations, Route 5 step (2) is conducted at 225-250° C., for about 2-3 hours. In some cases, the reaction time of 2-3 hours includes the time to ramp up to 225-250° C. In some cases, Route 5 step (2) is conducted at 250° C., and the total reaction time is about 2 hours, including the time to ramp up to temperature. It is desired to cool the reaction as quickly as possible to avoid formation of HMI 9, valeramide 11 or hexanamide 12. HMI 9 may form at temperatures of 160-180° C., so it is desired to cool the reaction to about 150° C. or cooler as quickly is possible. For example, it is desired to cool the reaction from 250° C. to about 150° C. in less than 20 minutes (e.g., about 10 minutes or less) to avoid formation of undesired side products.

In some cases in Route 5 step (2), the initial ammonia pressure is about 50-60 psi, the initial hydrogen pressure is about 600-1500 psi, the reaction temperature is 250° C., the reaction time is 2 hours (including time to ramp up from room temperature).

In certain embodiments of any synthesis routes described herein, the preferred double-bond isomer of muconic acid, dimethyl muconate and muconamide may be the trans,trans-isomer, then the cis,trans-isomer, and then the cis,cis-isomer (i.e., the order of preferred isomers may be trans,trans>cis, trans>cis,cis). One reason is that the trans,trans-isomer can be the most thermodynamically stable isomer of the three. For this reason, cis,cis-muconic acid 3a, as well as the cis,trans isomer 3b are sometimes converted to the trans,trans-muconic acid isomer 3c prior to further chemistry. The cis,cis- and cis,trans-double-bond isomers of DMM 6a and 6b can be sometimes converted to the trans,trans-double-bond isomer of DMM 6c. However, any of the isomers of muconic acid, dimethyl muconate and muconamide can be used for making caprolactam.

Another advantageous feature of this process is that caprolactam 1 can be synthesized directly from any of the muconic acid isomers (Q,Q-MA 3a-3c) in a one-pot process without using a dehydrating catalyst as is required in the process disclosed by U.S. Pat. No. 2,351,939.

Polyamides

Compounds prepared according to methods of the present invention can be used as monomers to prepare a variety of polymers such as polyamides. A polyamide is a polymer containing monomers of amides joined by peptide bonds. Polyamides are useful in a variety of commercial products, such as fibers, textiles, high performance plastics and the like, and may be prepared from a variety of amines and carboxylic acids. In general, the amide link can be produced from the condensation reaction between an amino group and a carboxylic acid, acid halide or carboxylate group. Polyamides are traditionally prepared from starting materials derived from petroleum feed stocks.

In certain embodiments, caprolactam prepared according to methods of the present invention can be subjected to a ring opening and polymerization reaction to form polyamide 6 (also known as nylon 6). Caprolactam can also be reacted with other compounds having amide-forming groups such as amine, carboxylic acid, acid halide and/or carboxylate groups, under suitable conditions to form various polyamides. Any processes for preparing such polyamides known in the art can be used, such as those disclosed in U.S. Pat. Nos. 6,846,868; 5,763,561; 6,291,633; 5,665,854; 5,194,577; 5,276,131; 5,218,082; 3,627,736 and 7,053,169, and Kirk-Othmer Encyclopedia of Chemical Technology, 3d Ed., 1982 John Wiley and Sons, Inc., Vol. 18, pp. 353-357, all of which are incorporated herein by reference in their entirety. The resulting polyamides contain at least about 6 carbons per monomer unit, and preferably at least about 6 carbon atoms that are from muconic acid precursors derived from renewable resources. In some embodiments, the resulting polyamides contain a detectable amount of $^{14}C$ and optionally up to about 1 part per trillion $^{14}C$.

Compounds having amide-forming groups can include aliphatic or aromatic dicarboxylic acids, or salts or halides or esters thereof, or any combination thereof. In some embodiments, dicarboxylic acids can be derived from renewable resources such as biomass. In some embodiments, suitable aliphatic dicarboxylic acids can contain from 3 to 30 carbon atoms, cyclic or non-cyclic, saturated or unsaturated, and optionally having one or more substituents such as halogen atoms, hydroxy groups, mercapto groups, alkyl groups containing 1 to 12 carbon atoms, alkenyl groups containing 2 to 12 carbon atoms, alkoxy groups containing from 1 to 12 carbon atoms, alkoxycarbonyl groups containing 2 to 24 carbon atoms, alkenyloxycarbonyl groups containing 4 to 24 carbon atoms, phenyl, benzyl, phenoxy, naphthyl or cyclohexyl groups, the ring moieties of which are optionally substituted by one or more substituents such as halogen atoms, hydroxy groups, alkyl groups containing 1 to 6 carbon atoms, or alkoxy groups containing 1 to 6 carbon atoms. Suitable aromatic dicarboxylic acids can contain any aryl group optionally having one or more substituents, and can include but not limited to isophthalic acid; terephthalic acid; 1,4-, 1,5-, 2,6-, and 2,7-naphthalenedicarboxylic acid; 4,4'-diphenyl ether dicarboxylic acid or 4,4'-benzophenonedicarboxylic acid; 4,4'-diphenyl sulfone dicarboxylic acid; 2-phenoxyterephthalic acid; 4,4-biphenyldicarboxylic acid; or mixtures thereof. Heterocyclic carboxylic acids can also be used, for example, those derived from pyridine, furan, thiophene, pyrrole and pyran, optionally having one or more substituents. Non-limiting examples of dicarboxylic acids are disclosed in U.S. Pat. No. 6,846,868, incorporated herein by reference. In some embodiments, a mixture of two of more dicarboxylic acids (e.g, a main dicarboxylic acid and one or more alternative dicarboxylic acid) can be used. For example, the amount of alternative dicarboxylic acids (e.g., isophthalic acid and/or 1,5-furandicarboxylic acid) may be about 40 mole percent or less based on the total moles of dicarboxylic acids, about 30 mole percent or less or about 20 mole percent or less.

Suitable compounds having amide-forming groups can include any aliphatic or aromatic diamines, or any combination thereof. Diamines can be any compound having two amine groups. In some embodiments, diamines can be derived from renewable resources such as biomass. In certain embodiments the diamines can have primary and/or secondary amine groups. Non-limiting examples of diamines include $C_{2-20}$ aliphatic, $C_{3-20}$ cycloaliphatic and $C_{6-20}$ aromatic diamines, optionally having one or more substituents. The aliphatic diamines can have straight or branched chains, cyclic or non-cyclic, saturated or unsaturated, and optionally having one or more substituents. Non-limiting examples of aliphatic diamines include those disclosed in U.S. Pat. No. 6,846,868, incorporated herein by reference, such as hexamethylenediamine, 1,9-nonane diamine and 2-methyl-1,8-octane diamine. Aromatic diamines can have one or more aryl group, optionally having one or more substituents. Non-limiting examples of aromatic diamines are disclosed in U.S. Pat. No. 6,846,868, incorporated herein by reference, such as p-phenylenediamine, m-phenylenediamine, xylylenediamine, 4,4'-diaminodiphenylsulfone and 4,4'-diaminodiphenylether. In some embodiments, a mixture of two of more diamines (e.g., an aliphatic diamine and non-aliphatic diamine) can also be used. For example, the amount of non-aliphatic diamines may be about 40 mole percent or less based on the total moles of diamines, about 30 mole percent or less or about 20 mole percent or less.

Compounds having amide-forming groups can also include aliphatic or aromatic amino carboxylic acids, or salts or halides or esters thereof. Amino carboxylic acids can have an amine group and a carboxylic acid group, and can contain from 3 to 30 carbon atoms, cyclic or non-cyclic, saturated or unsaturated, and optionally having one or more substituents such as halogen atoms, hydroxy groups, mercapto groups, alkyl groups containing 1 to 12 carbon atoms, alkenyl groups containing 2 to 12 carbon atoms, alkoxy groups containing from 1 to 12 carbon atoms, alkoxycarbonyl groups containing 2 to 24 carbon atoms, alkenyloxycarbonyl groups containing 4 to 24 carbon atoms, phenyl, benzyl, phenoxy, naphthyl or cyclohexyl groups, the ring moieties of which are optionally substituted by one or more substituents such as halogen atoms, hydroxy groups, alkyl groups containing 1 to 6 carbon atoms, or alkoxy groups containing 1 to 6 carbon atoms.

Non-limiting examples of diamines include hexamethylenediamine, 1,9-nonane diamine, 2-methyl-1,8-octane diamine, p-phenylenediamine, m-phenylenediamine, xylylenediamine, 4,4'-diaminodiphenylsulfone and 4,4'-diaminodiphenylether, each optionally having one or more substituents. Non-limiting examples of dicarboxylic acid include adipic acid, sebacic acid, glutaric acid, terephthalic acid, 2-methylterephthalic acid, isophthalic acid, naphthalenedicarboxlic acid, 1,5-furandicarboxylic acid, cyclopentane dicarboxylic, cyclopentene dicarboxylic, cyclohexane dicarboxylic, and cyclohexene dicarboxylic acids, each optionally having one or more substituents. No limiting examples of polyamide (PA) products include:

PA 6: $[NH—(CH_2)_5—CO]_n$ made from caprolactam;
PA 6/66: $[NH—(CH_2)_6—NH—CO—(CH_2)_4—CO]_n—[NH—(CH_2)_5—CO]_m$ made from caprolactam, hexamethylenediamine and adipic acid; hexamethylenediamine can be provided by any available source, including but not limited to the methods of preparation disclosed in PCT International Patent Application entitled "Process for Preparing Hexamethylenediamine and Polyamides Therefrom", Attorney Docket No. 136556-013002/PCT, filed on Apr. 9, 2012, incorporated herein by reference.

In some examples, polyamides can be prepared in a multistep reaction sequence. In general, one or more dicarboxylic acids (or diesters or other derivatives) can be contacted with one or more diamines (e.g., HMDA) to form a salt. The salt can then be subject to a polycondensation step to form a prepolymer. The prepolymer can be optionally subjected to a solid phase polymerization, solution polymerization, or melt polymerization to form a polyamide of a desired molecular weight.

In the salt formation step, one or more diamines and dicarboxylic acids (or diesters) are contacted. This step can be conducted in water, for instance from 20 to 150 weight percent of water based on the weight of the reactants. Optionally this step is conducted in the absence of free oxygen or under an inert atmosphere, e.g., under nitrogen. The one or more diamines and one or more dicarboxylic acids are preferably contacted at water reflux, for example, at about 90° C. to 100° C. The reaction can be performed at superatmospheric pressures, e.g., about 100 kPa to about 1000 kPa, about 200 kPa to about 600 kPa, or greater or less. Preferably the volatiles are removed during this process and if one or more of reactants volatilize away during the condensation step additional quantities of that reactant(s) may need to be added to maintain the desired stoichiometry. The formed salt may be recovered by cooling to precipitate the salt and performing a standard separation, such as filtration or centrifugation. Impurities may be removed by contacting with an adsorbant such as active carbon. Alternatively the formed salt may be exposed to polycondensation conditions without recovery from the reaction medium.

Next, during polycondensation of the salt to a prepolymer, the salt can be exposed to temperatures at which the salt condenses to form an amide linkage. In some embodiments, the reactants are contacted in an aqueous reaction mixture at a temperature of about 200° C. to about 330° C., about 250° C. to about 310° C., about 270° C. to about 300° C., or greater or less. This contacting step can be conducted in water, for instance from about 20 to about 150 weight percent of water based on the weight of the salt. The reaction can be conducted in the absence of free oxygen or under an inert atmosphere, e.g., under nitrogen. The reaction can be performed at superatmospheric pressures, e.g., about 100 kPa to about 1000 kPa, about 200 kPa to about 600 kPa, or greater or less. Once the desired molecular weight has been achieved, water can be removed and the product can be granulated or transferred to an extruder.

If the resulting product does not have the desired molecular weight it can be subjected to solid state or melt polymerization. In this step the polymer can be exposed to conditions under which the polymer continues to polymerize. This can be performed at reduced pressure and/or under an inert atmosphere. The polymerization can be conducted in a polymerization apparatus, for example, a batch-type reactor, a single-tank or multi-tank continuous polymerization apparatus, a tubular continuous polymerization apparatus, or a kneading reaction extruder. The polymerization can be conducted with agitation. In a solid state polymerization the agitation is typically performed by an impeller. In melt polymerization the polymer can be fed through an extruder where the screws of the extruder can provide the agitation. The reaction temperature can be about 200° C. to about 370° C., about 250° C. to about 300° C., about 270° C. to about 280° C., or greater or less. The polymerization step may be performed in the presence of a phosphorous catalyst or any other suitable catalyst known in the art. Exemplary phosphorous catalysts include phosphoric acid, phosphorous acid or hypophosphoric acid or a salt or ester thereof, such as those disclosed in U.S. Pat. No. 6,846,868, incorporated herein by reference. The phosphorous catalyst can be used in a sufficient amount such that a reasonable rate of condensation and reasonable yield are achieved, for example, in an amount of about 0.01 to 5 wt %, about 0.05 to 2 wt %, about 0.07 to 1 wt %, or greater or less. The reaction mixture may also contain one or more monoamines or monocarboxylic acids to control the molecular weight of the polyamide (e.g., by adding to the end of the extending polymer chain thereby stopping the polymerization). Exemplary monoamines or monocarboxylic acids are disclosed in U.S. Pat. No. 7,053,169, incorporated herein by reference.

In certain examples where nylon 6 is the desired product, caprolactam may be heated to about 200° C. to about 300° C., about 250° C. to about 270° C., or greater or less. The reaction can be conducted in an inert atmosphere, e.g., nitrogen. After the ring breaks and undergoes polymerization till desired molecular weight is reached, the molten mass can be passed through spinnerets to form fibers of nylon 6.

The polyamides of the present invention can be formulated with known additives. For example, the polyamides are formulated to contain one or more copper and/or alkali metal stabilizers as disclosed U.S. Pat. Nos. 6,846,868 and 5,763,561, both incorporated herein by reference. Other additives such as fillers, pigments, stabilizers, flame retardants, nucleating agents, lubricants, impact modifiers, thermoplastic polymers and the like are disclosed in U.S. Pat. Nos. 5,194,577; 6,846,868; and 6,291,633, all incorporated herein by reference. The polyamide compositions of the invention can be formed by blending in a suitable mixer or extruder.

The polyamides can be formed into fibers, films or molded products using known processes. The polyamides can be formed into the desired shape by thermoforming, melt extrusion, injection molding and the like. The polyamides can be formed or molded into automobile engine parts, electrical connectors, electrical equipment parts, etc. Specific examples of these molded objects include mechanism elements such as an oil strainer, timing chain cover, rocker cover, timing chain tensioner, thrust washer, power steering tank, oil level gauge, brake fluid subtank, brake master cylinder, brake piston rod, automatic-transmission stator, bearing retainer, governor gear, and sensor, electrical equipment parts such as a relay box and connector, and electrical/electronic parts such as a terminal board, connector, and relay.

EXAMPLES

This invention will be further clarified by a consideration of the following examples, which are intended to be purely exemplary of the present invention. Those of ordinary skill in the art will readily recognize a variety of non-critical parameters that could be changed or modified to yield essentially similar results.

Materials and Methods

Solvents were used as commercially supplied unless otherwise noted.

Tetrahydrofuran (THF) was dried by distillation in the presence of sodium and benzophenone under a nitrogen atmosphere.

Muconic acid double-bond isomers (Q,Q-MA 3a-3c) were obtained from a fermentation process using sugar from renewable biomass feedstock as described in detail below.

Solvents were removed under reduced pressure by rotary evaporation, and residual solvent was removed by vacuum pump at less than 2 mmHg.

Analytical thin-layer chromatography (TLC) was performed on E. Merck precoated TLC plates (silica gel 60 F-254, layer thickness 0.2 mm).

Melting points were determined using a MeI-Temp II melting-point apparatus and are uncorrected.

Nuclear magnetic resonance (NMR) spectra were obtained on a Varian spectrometer; chemical shifts are expressed as parts per million downfield from tetramethylsilane.

Unless otherwise specified, the following analytical methods were used. High Pressure Liquid Chromatography (HPLC) was performed using Agilent 1100 series system using the following method: Column=Prevail Organic Acid (150 mm×4.6 mm, Grace Davison Discovery Sciences). Mobile Phase: potassium phosphate buffer (25 mM, pH 1.5): acetonitrile (85:15). Detection wavelength=257 nm.

Gas Chromatography Mass Spectra (GCMS) was analyzed using Agilent 6890 GC system with Agilent 5973 inert Mass Selective Detector and the following method: Column=J&W Sci 112-2132; 220° C. Max CAM Capillary 30.0 m×250 μM×0.25 μm nominal. Temperature profile=90° C. initially and hold for 2 min; ramp up to 200° C. at a rate of 10° C./min and hold for 15 min. Inlet temperature=250° C.

Caprolactam yields in the conversion of muconic acid or muconolactone to caprolactam were determined using the following HPLC method: 16% ACN/84% 0.025M Potassium Phosphate Buffer pH 1.7 isocratic, Zorbax SBAQ 4.6×150 mm column, detector wavelength=214 nm, retention time=3.49 min.

Adipamide yields in the conversion of muconic acid or muconolactone to caprolactam were determined using the following HPLC method: 1% Methanol 99% 0.025M Potassium Phosphate buffer pH 1.7 with a step gradient at end to 30% Methanol to wash the column, Zorbax SBAQ 4.6×150 mm column, detector wavelength=214 nm, retention time=4.72 min.

HMI yields in the conversion of muconic aid or muconolactone to caprolactam were determined on the following HPLC method: 95% 0.03M Ammonium Phosphate Buffer pH 3, 5% Acetonitrile, Zorbax 300 SCX 4.6×150 mm 5 micron column, Agilent part#883952-704, Refractive Index Detector, retention time=4.56 min.

The invention will be further clarified by a consideration of the following examples, which are intended to be purely exemplary of the present invention. The lettered Examples are synthesis of starting materials or comparative examples, and the numbered Examples are those examples of the present invention.

Starting Materials

The present invention for the production of biomass-derived caprolactam 1 uses muconic acid as the starting material. Muconic acid used in the methods described herein can be obtained from any available source or prepared by any technique known by or apparent to one of skill in the art. In some cases, muconic acid is derived from a microbial organism that has been modified to produce muconic acid. Microbially-derived muconic acid may contain any one of or any combination of the cis,cis-, cis-trans-, and trans,trans-isomers of muconic acid. In some instances, the most prevalent isomer in microbially-derived muconic acid is cis,cis-muconic acid. In some instances, the most prevalent isomer in microbially-derived muconic acid is cis,trans-muconic acid. In some instances, the most prevalent isomer in microbially-derived muconic acid is trans,trans-muconic acid. The muconic acid present in a cell culture medium or fermentation broth used in the microbial synthesis may be used as-is, purified, or isolated before undergoing amidation reaction. Non-limiting examples of purification or isolation methods include extraction, washing, filtration, centrifuge, and combinations thereof.

In certain variations, muconic acid is microbially synthesized from readily available carbon sources capable of biocatalytic conversion to erythrose 4-phosphate (E4) and phosphoenolpyruvate (PEP) in microorganisms having a common pathway of aromatic amino acid biosynthesis. Carbon sources used in the synthesis are advantageously renewable, being derived from starch, cellulose and sugars found, for example, in corn, sugar cane, sugar beets, wood pulp and other biomass. One carbon source that can be used to make muconic acid is D-glucose.

Any suitable method for microbial synthesis of muconic acid may be used. A host microbial organism is selected such that it produces the precursor of a muconate pathway, either as a naturally produced molecule or as an engineered product that produces the precursor or increases production of the precursor naturally produced by the host organism. In some cases, an engineered organism is generated from a host that contains the enzymatic capability to synthesize muconate. Increased synthesis or accumulation of muconate can be accomplished by overexpression of nucleic acids encoding one or more muconate pathway enzymes or proteins. Engineered organisms may be designed to produce muconate through overexpression of any number of the nucleic acids encoding muconate biosynthetic pathway enzymes or proteins.

In certain embodiments, MA can be produced via fermentation of sugars derived from biomass. The conversion of biomass to cis,cis-muconic acid can be found in U.S. Pat. Nos. 4,879,987 and 5,487,987, both of which patents are incorporated herein by reference in their entirety.

Host microbial organisms suitable for synthesizing muconic acid may be selected from genera possessing an endogenous common pathway of aromatic amino acid biosynthesis. In certain embodiments, the host cells are recombinantly modified to produce the muconic acid, or a precursor thereof. Illustrative examples of suitable host cells include any archae, prokaryotic, or eukaryotic cell. Examples of an archae cell include, but are not limited to those belonging to the genera: *Aeropyrum, Archaeglobus, Halobacterium, Methanococcus, Methanobacterium, Pyrococcus, Sulfolobus*, and *Thermoplasma*. Illustrative examples of archae strains include but are not limited to: *Aeropyrum pernix, Archaeoglobus fulgidus, Methanococcus jannaschii, Methanobacterium thermoautotrophicum, Pyrococcus abyssi, Pyrococcus horikoshii, Thermoplasma acidophilum, Thermoplasma volcanium*.

Examples of a procaryotic cell include, but are not limited to those belonging to the genera: *Agrobacterium, Alicyclobacillus, Anabaena, Anacystis, Arthrobacter, Azobacter, Bacillus, Brevibacterium, Chromatium, Clostridium, Corynebacterium, Enterobacter, Erwinia, Escherichia, Lactobacillus, Lactococcus, Mesorhizobium, Methylobacterium, Microbacterium, Phormidium, Pseudomonas, Rhodobacter, Rhodopseudomonas, Rhodospirillum, Rhodococcus, Salmonella, Scenedesmun, Serratia, Shigella, Staphlococcus, Strepromyces, Synnecoccus*, and *Zymomonas*.

Illustrative examples of prokaryotic bacterial strains include but are not limited to: *Bacillus subtilis, Bacillus amyloliquefacines, Brevibacterium ammoniagenes, Brevibacterium immariophilum, Clostridium beigerinckii, Enterobacter sakazakii, Escherichia coli, Lactococcus lactis, Mesorhizobium loti, Pseudomonas aeruginosa, Pseudomonas mevalonii, Pseudomonas pudica, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella sonnei, Staphylococcus aureus*, and the like.

In general, if a bacterial host cell is used, a non-pathogenic strain is preferred. Illustrative examples of non-pathogenic strains include but are not limited to: *Bacillus subtilis, Escherichia coli, Lactibacillus acidophilus, Lactobacillus helveticus, Pseudomonas aeruginosa, Pseudomonas mevalonii, Pseudomonas pudita, Rhodobacter sphaeroides, Rodobacter capsulatus, Rhodospirillum rubrum*, and the like.

Examples of eukaryotic cells include but are not limited to fungal cells. Examples of fungal cell include, but are not limited to those belonging to the genera: *Aspergillus, Candida, Chrysosporium, Cryotococcus, Fusarium, Kluyveromyces, Neotyphodium, Neurospora, Penicillium, Pichia, Saccharomyces, Trichoderma* and *Xanthophyllomyces* (formerly *Phaffia*).

Illustrative examples of eukaryotic strains include but are not limited to: *Aspergillus nidulans, Aspergillus niger, Aspergillus oryzae, Candida albicans, Chrysosporium lucknowense, Fusarium graminearum, Fusarium venenatum, Kluyveromyces lactis, Neurospora crassa, Pichia angusta, Pichia finlandica, Pichia kodamae, Pichia membranaefaciens, Pichia methanolica, Pichia opuntiae, Pichia pastoris, Pichia pijperi, Pichia quercuum, Pichia salictaria, Pichia thermotolerans, Pichia trehalophila, Pichia stipitis, Streptomyces ambofaciens, Streptomyces aureofaciens, Streptomyces aureus, Saccaromyces bayanus, Saccaromyces boulardi, Saccharomyces cerevisiae, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus, Trichoderma reesei* and *Xanthophyllomyces dendrorhous* (formerly *Phaffia rhodozyma*).

In general, if a eukaryotic cell is used, a non-pathogenic strain is preferred. Illustrative examples of non-pathogenic strains include but are not limited to: *Fusarium graminearum, Fusarium venenatum, Pichia pastoris, Saccaromyces boulardi*, and *Saccaromyces cerevisiae*.

The muconic acid (Q,Q-MA) used to prepare caprolactam 1 can be present as the cis,cis-, cis,trans-, or trans,trans-double-bond isomer. In some variations, the methods may comprise isomerizing the muconic acid (or muconic acid ester, see below for details) prior to the amidation reaction (to make Q,Q-MCA). In some instances, it may be desired to isomerize muconic acid to form predominantly the cis,cis-, cis,trans-, or trans,trans-isomer. For example, in some cases muconic acid produced via microbial synthesis may be the cis, cis-muconic acid isomer or a mixture of cis,cis-muconic acid and cis,trans-muconic acid, and it may be desired to isomerize the cis,cis-muconic acid (or ester) to form cis,trans-muconic acid (or ester) or trans,trans-muconic acid (or ester), or to isomerize cis,trans-muconic acid (or ester) to form cis, cis-muconic acid (or ester) or trans,trans-muconic acid (or ester) before the amidation reaction. Isomerization may occur using any suitable isomerization conditions and appropriate isomerization conditions and catalysts (if needed). For example, the cis,cis-isomer can be isomerized to the cis,trans-isomer in boiling water without a need for a catalyst. In some variations, iodine is used as a catalyst for isomerization, and in some variations iodine-catalyzed photochemical isomerization of cis,cis- or cis,trans-isomers to trans,trans-isomers can be used. Non-limiting examples of methods for isomerizing muconic acid are provided in International Patent Publication No. WO 2010/148063 and in Elvidge J A et al., Journal of the Chemical Society, Chemical Society, Letchworth, G B, 1 Jan. 1950 (1950-01-01), pages 2235-2241, each of which is incorporated by reference herein in its entirety. It should be understood that esterification of muconic acid may occur prior to isomerization to form desired isomers, or isomerization to form desired isomers may occur prior to esterification.

For example, the cis,cis-MA 3a may be converted to cis, trans-MA 3b in a discrete step. In such a discrete step, the cis,cis-MA 3a can be dissolved or dispersed in water and exposed to elevated temperatures to convert the cis,cis-MA 3a to the cis,trans-MA double-bond isomer 3b. Small amounts of other acids, for example sulfuric acid, can be added to accelerate the isomerization. Temperatures which may be used for this process steps include any temperature at which the isomerization proceeds, this process step being performed as long as required to convert the desired amount of cis, cis-MA 3a to the cis,trans-MA double-bond isomer 3b.

Both cis,cis-MA 3a and cis,trans-MA 3b may be converted to trans,trans-MA 3c with one or more isomerization catalysts, a source of ultraviolet radiation or both, in solvent to form the trans,trans-MA 3c.

Muconic acid can be converted to muconic acid esters by any method apparent to those of skill in the art. Muconic acid esters may also be obtained from any source. In some embodiments, muconic acid esters are prepared by esterification of muconic acid. Any suitable esterification method known in the art may be used to obtain the desired monoester or diester. Muconic acid may be contacted with an esterifying agent under conditions suitable to form the desired ester. Non-limiting examples of esterifying agents include alkanols (e.g., $C_1$-$C_{10}$ alkanols, polyols, polyalkylene glycols having one or more hydroxyl groups and one or more ether groups, aryl alcohols (e.g., phenol or isomers of dihydroxyl benzene), and aryl substituted alcohols (e.g., benzyl alcohol). In some cases, muconic acid is contacted with one or more esterifying agents in the presence of one or more acids. Non-limiting examples of suitable acids include sulfuric acid, nitric acid, phosphoric acid, hydrochloric acid, p-toluene sulfonic acid, and Lewis acids. The esterification reaction may be carried out in the presence of acid at an elevated temperature, e.g., about 50° C., 60° C., 70° C., 80° C., 90° C., 100° C., 110° C., 120° C., 130° C., 140° C., or 150° C. As another example, muconic acid may be esterified by reacting with an alcohol in the presence of a base (e.g., pyridine, a tertiary amine, or aqueous NaOH). Further non-limiting examples of esterification reactions for muconic acid are provided in International Patent Publication Nos. WO 2010/148063, WO 2010/148080, WO 2010/148049, WO 2010/148081 and WO 2010/148070, all of which applications are incorporated herein by reference in their entirety.

Muconic acid ester can have the formula $R^1OOC$—C=C—C=C—$COOR^2$, where $R^1$ and $R^2$ can be the same or different, and $R^1$ and $R^2$ are each individually any alkyl, alkenyl, alkynyl, aryl, cyclalkyl, cycloalkenyl, alkaryl and aralkyl group that is unsubstituted or substituted. In certain variations, one or both of $R^1$ and $R^2$ are $C_1$-$C_{10}$ alkyl groups. For example, one or both of $R^1$ and $R^2$ may be selected from the group consisting of methyl, ethyl, propyl, isopropyl, n-butyl, isobutyl, t-butyl, n-pentyl, isopentyl, 2-methylpentyl, 3-methylpentyl, 2-ethylbutyl, n-hexyl, isohexyl, 2-methylhexyl, 3-methylhexyl, 4-methylhexyl, n-heptyl, isoheptyl, 2-methylheptyl, 3-methylheptyl, 4-methylheptyl, 5-methylheptyl, 2-ethylhexyl, 3-ethylhexyl, 4-ethylhexyl, 5-ethylhexyl, 6-ethylhexyl, n-octyl, isooctyl, 2-methyloctyl, 3-methyloctyl, 4-methyloctyl, 5-methyloctyl, 6-methyloctyl, 2-ethylheptyl, 3-ethylheptyl, 4-ethylheptyl, 5-ethylheptyl, n-nonyl, isononyl, 2-methylnonyl, 3-methylnonyl, 4-methylnonyl, 5-methylnonyl, 6-methylnonyl, 7-methylnonyl, 2-ethyloctyl, 3-ethyloctyl, 4-ethyloctyl, 5-ethyloctyl, 6-ethyloctyl, n-decyl, and isodecyl. In one embodiment, both $R^1$ and $R^2$ can be methyl and the ester is dimethyl muconate (DMM).

Any muconic acid ester can replace DMM in Route 3 or 4 in Scheme 3. The following lettered Examples are directed to the preparation of cis,trans- and trans,trans-isomers of muconic acid from the cis, cis-isomer, of the various double-bond isomers of dimethyl muconate (Q,Q-DMM 6a-6c) and of muconamide (Q,Q-MCA 4a-4-c), and of the double bond isomers of muconolactone 5.

Example A

Isomerization of cis,cis-Muconic Acid [cis,cis-Ma 3a] to cis,trans-Muconic Acid [cis,trans-MA 3b] in Water

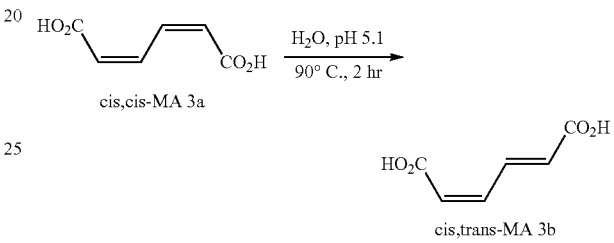

cis,cis-MA 3a (265 g) produced by fermentation of sugars derived from renewable biomass was suspended in water (2 L) and the pH of the solution was adjusted to 5.1 with 10 M of NaOH (250 mL). The mixture was heated at 90° C. for 2 hr. Samples were taken at T=0 min; T=60 min; and T=120 min and analyzed by HPLC. After 2 hr of heating at 90° C., the reaction mixture was treated with charcoal (20 g) for 30 min and the hot solution was filtered through a thin bed of filter aid. The solution was adjusted to pH 2 with concentrated sulfuric acid (50 mL) and allowed to cool to 0° C. in an ice-bath. The precipitate cis,trans-muconic acid was obtained by filtration and dried under reduced pressure to yield 71 g of cis,trans-MA 3b as light yellow solid. The filtrate was concentrated to 600 mL and allowed to incubate overnight at 0° C. The precipitated was filtered and dried to yield an additional 152 g of cis,trans-MA 3b (overall yield of 84%) whose $^1H$ and $^{13}C$ NMR data are:

$^1$H-NMR (500 MHz, DMSO-d6): δ 8.20 (ddd, J=15.6, 11.7, 1 Hz, 1H), 6.80 (dt, J=11.7, 1 Hz, 1H), 6.22 (dt, J=15.6, 0.6 Hz, 1H), 6.00 (td, J=11.1, 0.6 Hz, 1H); and $^{13}$C-NMR (125 MHz, DMSO-d6): δ 167.1, 166.6, 140.1, 138.2, 129.5, 125.5.

Example B

Isomerization of cis,trans-Muconic Acid [cis,trans-MA 3b] to trans,trans-Muconic Acid [trans,trans-MA 3c] in Tetrahydrofuran (THF)

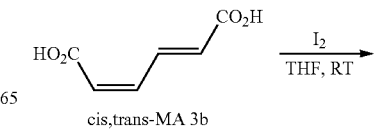

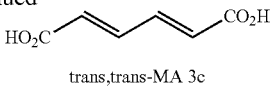

trans,trans-MA 3c cis,trans-MA 3b (19 g, 133.8 mmol) was dissolved in THF (250 mL) at RT and a crystal of iodine (160 mg, 0.63 mmol) was added. The reaction mixture was heated at reflux for 4 hr and the precipitate was filtered, washed with acetonitrile and dried under reduced pressure to yield 16 g of trans,trans-MA 3c, (84% yield) whose $^1$H and $^{13}$C NMR data are:

$^1$H-NMR (300 MHz, DMSO-d6) δ 12.59 (s, 2H), 7.28 (dd, J=6.9, 1.8 Hz, 2H), 6.30 (dd, J=6.9, 1.8 Hz, 2H); and $^{13}$C-NMR (75 MHz, DMSO-d6): δ 166.8, 140.8, 129.1.

Example C

Synthesis of cis,cis-Dimethyl Muconate [cis,cis-DMM 6a] from cis,cis-Muconic Acid [cis,cis-MA 3a]

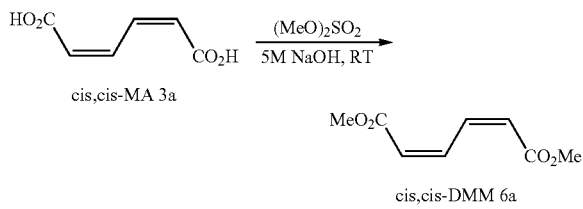

cis,cis-MA 3a (20 g, 140.8 mmol) was suspended in 5 M NaOH (84 mL) and allowed to stir at RT for 1 hr under nitrogen atmosphere. Dimethyl sulfate was then added dropwise and the reaction mixture was allowed to stir at RT under nitrogen atmosphere for 8 hr. The reaction mixture was extracted with ethyl acetate (3×, 200 mL). The organic fractions were combined, washed with 1 M NaOH (6×, 30 mL), then with water (1×, 30 mL), and then with brine (1×, 40 mL), dried with MgSO$_4$ and concentrate to yield 9.0 g of cis,cis-DMM 6a (38% yield) whose $^1$H and $^{13}$C NMR data are:

$^1$H-NMR (500 MHz, DMSO-d6): δ 7.74 (dd, J=8.25, 2.5 Hz, 2H), 6.12 (dd, J=8.25, 2.5 Hz, 2H), 3.68 (s, 3H); and $^{13}$C-NMR (125 MHz, DMSO-d6): δ 165.4, 137.1, 124.2, 51.4.

Example D

Synthesis of cis,trans-Dimethyl Muconate [cis,trans-DMM 6b] from cis,trans-Muconic Acid [cis,trans-MA 3b]

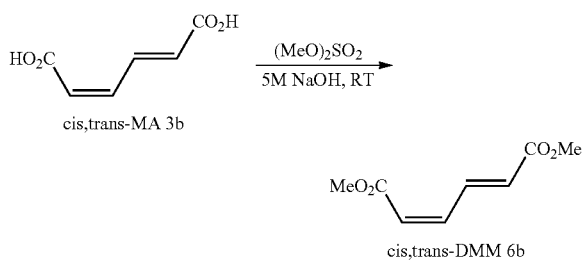

Part A: cis,trans-MA 3b (20 g, 140.8 mmol) was suspended in 5 M NaOH (84 mL) and allowed to stir at RT for 1 hr under nitrogen atmosphere. Dimethyl sulfate was then dropwise-added and the reaction mixture was allowed to stir at RT under nitrogen atmosphere for 8 hr. The reaction mixture was extracted with ethyl acetate (3×, 200 mL). The organic fractions were combined, washed with 1 M NaOH (6×, 30 mL), then with water (1×, 30 mL), and then with brine (1×, 40 mL), dried with MgSO$_4$ and concentrated to yield 7.5 g (31%) of white solid, cis,trans-DMM 6b. whose $^1$H and $^{13}$C NMR data are:

$^1$H-NMR (500 MHz, DMSO-d6): δ 8.23 (ddd, J=15.5, 11.5, 1 Hz, 1H), 6.90 (dt, J=11.5, 0.5 Hz, 1H), 6.90 (dt, J=11.5, 0.5 Hz, 1H), 6.37 (td, J=15.5, 0.5 Hz, 1H), 6.09 (dt, J=11.5, 1.0 Hz, 1H), 3.70 (s, 3H), 3.69 (s, 3H); and $^{13}$C-NMR (125 MHz, DMSO-d6): δ 165.9, 165.3, 140.7, 138.1, 128.7, 124.1, 51.7, 51.5.

Part B: Alternatively, cis,trans-DMM 6b can be synthesized by refluxing cis,trans-MA 3b in MeOH with a catalytic amount of sulfuric acid according to the following procedure: cis,trans-MA 3b (50.3 g, 0.35 mol) was dissolved in MeOH (1500 mL) along with concentrated sulfuric acid (2 mL, 0.037 mol). The resulting solution was refluxed for 18 hr and monitored by HPLC. Once the conversion of cis,trans-MA 3b to cis,trans-DMM 6b was completed as detected by HPLC, the reaction was cooled to RT and concentrated until white solid began precipitating from the solution, whereupon the reaction mixture was cooled to 0° C. The cis,trans-DMM 6b was obtained by filtration, washed with cold THF and dried under reduced pressure to provide a yield of 93%. The product was analyzed by NMR and HPLC, which indicated that it is pure cis,trans-DMM 6b. This process provides an alternative approach to the synthesis of cis,trans-DMM 6b that avoids the use dimethyl sulfate as methylating agent.

Example E

Synthesis of trans,trans-Dimethyl Muconate [trans,trans-DMM 6c] from trans,trans-Muconic Acid [trans,trans-MA 3c]

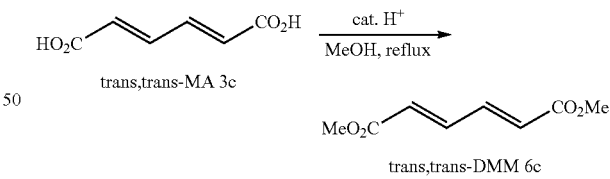

trans,trans-MA 3c (16 g, 112.6 mmol) was suspended in MeOH (500 mL) along with catalytic amount of sulfuric acid (0.5 mL). The reaction mixture was brought to reflux for 72 hr and then allowed first to cool to RT and then to 0° C. in an ice-bath. White needle crystals formed in the process were collected by filtration, dried under reduced pressure to yield 19 g (99% yield) of trans,trans-DMM 6c whose $^1$H and $^{13}$C NMR data are:

$^1$H-NMR (500 MHz, DMSO-d6): δ 7.39 (dd, J=11.5, 3.0 Hz, 2H), 6.47 (dd, J=11.5, 3.0 Hz, 2H), 3.69 (s, 3H); and $^{13}$C-NMR (125 MHz, DMSO-d6): δ 165.8, 141.1, 128.1, 51.6.

Example F

Preparation of cis,cis-Muconamide [cis,cis-MCA 4a] from cis,cis-Dimethyl Muconate [cis,cis-DMM 6a]

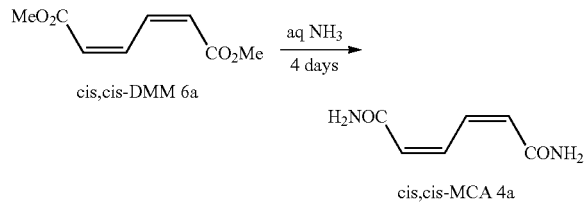

cis,cis-DMM 6a (6.2 g, 36.4 mmol) was suspended in aq. $NH_3$ (50 mL) and the mixture was allowed to stir at RT for 4 days. A white precipitate was formed and obtained by filtration, dried under reduced pressure to yield 3.0 g (59% yield) of white solid cis,cis-MCA 4a whose $^1H$ and $^{13}C$ NMR data are:

$^1$H-NMR (300 MHz, DMSO-d6): δ 7.72 (dd, J=8.1, 2.1 Hz, 2H), 7.57 (s, 2H), 7.10 (s, 2H), 5.91 (dd, J=8.2, 2.1 Hz, 2H); and $^{13}$C-NMR (75 MHz, DMSO-d6): δ 167.1, 134.3, 126.3.

m.p.=244° C. to 246° C. (decomposed).

Example G

Preparation of cis,trans-Muconamide [cis,trans-MCA 4b] from cis,trans-Dimethyl Muconate [cis,trans-MCA 6b]

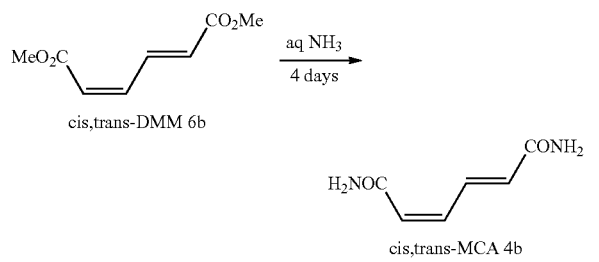

cis,trans-DMM 6b (5 g, 29.5 mmol) was suspended in aq. $NH_3$ (50 mL) and the mixture was allowed to stir at RT for 4 days. The reaction mixture was concentrated until white solid began to precipitate out of the solution. The concentrated solution was chilled in an ice-bath for 1 hr and the precipitate was obtained by filtration, dried under reduced pressure to yield 2.5 g (60% yield) of cis,trans-MCA 4b, as a white solid, whose $^1H$ and $^{13}C$ NMR data are:

$^1$H-NMR (300 MHz, DMSO-d6) δ 8.22 (ddd, J=15.5, 11.7, 0.9 Hz, 1H), 7.57 (d, J=4.8 Hz, 2H), 7.14 (d, J=10.5 Hz, 2H), 6.50 (t, J=11.7 Hz, 1H), 6.13 (d, J=15.3 Hz, 1H), 5.95 (d, J=11.4 Hz, 1H); and $^{13}$C-NMR (75 MHz, DMSO-d6): δ 166.8, 166.4, 137.1, 135.2, 130.9, 127.0.

m.p.=190° C. to 192° C. (decomposed).

Example H

Preparation of trans,trans-Muconamide [trans,trans-MCA 4a] from trans,trans-Dimethyl Muconate [trans,trans-DMM 6c]

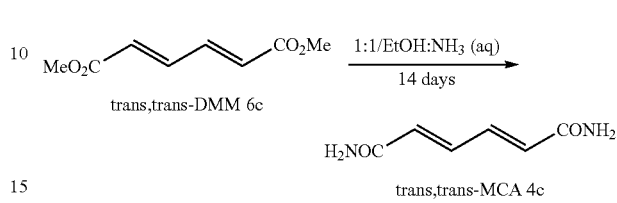

trans,trans-DMM 6c (27 g, 159 mmol) was suspended in aq. $NH_3$ (200 mL) and EtOH (200 mL) and the mixture was allowed to stir at RT for 14 days. A white precipitate formed and was filtered, washed with MeOH, and dried under reduced pressure to provide 17.23 g (77% yield) of trans,trans-MCA 4c as white solid, whose $^1H$ and $^{13}C$ NMR data are:

$^1$H-NMR (300 MHz, DMSO-d6): δ 7.62 (s, 2H), 7.18 (s, 2H), 7.08 (dd, J=11.3, 3.3 Hz, 2H), 6.29 (dd, J=11.3, 3.3 Hz, 2H); and $^{13}$C-NMR (75 MHz, DMSO-d6): δ 166.2, 136.8, 130.8.

m.p.=276° C. to 280° C. (decomposed).

Example I

Preparation of Muconolactone 5 from cis,trans-Muconic Acid [cis,trans-MA 3b]

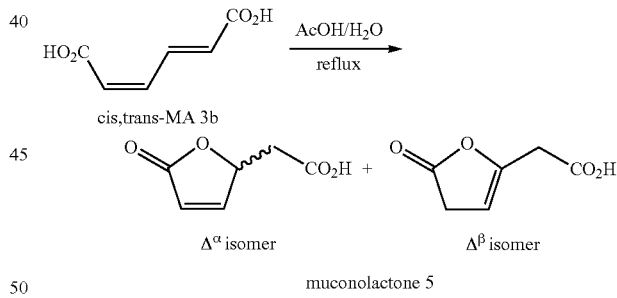

This reaction conditions used were modified from Elvidge et al, *J. Chem. Soc.* 1950, 2228.

Aqueous acetic acid (1/2 v/v AcOH/$H_2O$, 45 ml) containing purified cis,trans muconic acid 3b (2.0 g, 14.1 mmol) was heated to reflux for 20 hr. Upon cooling to RT, concentration on a rotavap and drying under high vacuum (~1 mm) overnight, a yellow solid contaminated by a small amount of colorless oil was present. All material (1.8 g) was suspended in a warm mixture of $CH_2Cl_2$ (about 23 mL) and i-PrOH (about 5 mL), whereupon almost all material dissolved, and filtered through cotton in a pipette. The filtrate was overlayered with hexanes (~60 mL) and stored at RT. After 2 days, a small amount of white powder and large colorless crystals were present. The mother liquid was decanted and all solid dried (1.1 g, 55%) under high vacuum. The material was found to consist of 79% $\Delta^\alpha$-double bond isomer of muconolactone 5 and 20% of $\Delta^\beta$-double bond isomer of muconolactone 5. The $^1$H data are:

$^1$H NMR (300 MHz, DMSO-$D_6$) of $\Delta^\alpha$: $\delta$=12.62 (br s, 1H, $CO_2H$), 7.80 (dd, 1H, J=5.7, 1.5 Hz, $H^\beta$), 6.24 (dd, 1H, J=5.7, 2.0 Hz, $H^\alpha$), 5.39 (m, 1H, $H^\gamma$), 2.84 ppm (dd, 1H, J=16.5, 4.9 Hz, $CH_2$), and 2.51 ppm (dd, 1H, J=16.5, 8.2 Hz, $CH_2$), which data are in agreement with the reported values [Hizuka, Hayashi, Kamashita, Suemune, & Sakai, Chem. Pharm. Bull. 1988, 36, 1550-1553.]

Exemplary Reactions

The following numbered Examples illustrate various reaction conditions for preparing caprolactam 1.

Example 1

Conversion of trans,trans-muconamide 4c to Caprolactam 1

A series of reactions were performed in the general manner described immediately below for the conversion of trans, trans-MCA 4c to caprolactam 1.

A pressure reactor (Model 4575/76 HP/HT Pressure Reactor from Parr Instrument Company, equipped with stirrer, gas inlet and dip-tube) was charged with 1 g of trans,trans-MCA 4c plus 100 mL of solvent. To this was added the catalyst, the reactor closed, and hydrogen gas charged to the desired pressure. Following this, anhydrous ammonia was optionally charged. The reactor was then heated to the desired temperature and samples taken at desired times using the dip-tube. Analysis was performed to determine the production of caprolactam 1, unreacted starting material 4c, and the anticipated by-products adipamide 7 and hexamethylenediamine (HMDA) 8.

Individual variations for specific reactions are further described below, and the results are summarized in the Table 1.

When the reaction was carried out at low hydrogen pressure (200-300 psi), adipamide was detected as the only product, (entry 1 and 2). When the reactions were carried out in the absence of ammonia (entries 1 to 4), only very low amounts of HMDA 8 or caprolactam 1 were observed. When the reaction was carried out in the presence of ammonia using THF as reaction solvent, a 33% yield of caprolactam 1 and a 5% yield of HMDA 8 were observed (entry 5).

Solvents such as t-butyl methyl ether (TBME) (entry 6), was also screened, but under the conditions tested, no HMDA 8 was detected and only trace amount of caprolactam 1 observed.

The catalyst loading was also varied (entries 7 to 10). When 5 wt % copper chromite catalyst was used, yields of 5% caprolactam 1 and 33% adipamide 7 were obtained with no trace of HMDA 8 (entry 7). Using 10 wt % copper chromite, yields of 13% caprolactam 1 and 30% adipamide 7 were observed, again with no trace of HMDA 8 (entry 8). At 45 wt % catalyst loading, a 7% yield of HMDA 8 was observed and no other desired products were detected (entry 9), and at 99 wt % catalyst loading a yield of 6.7% HMDA 8 was achieved (entry 10).

When the reaction was carried out at 150° C. (entry 11), only a trace of caprolactam 1 was observed but with a 76% yield of adipamide 7.

When the $H_2$ pressure was reduced to 500 psi (entry 12) while keeping the reaction temperature at 250° C., only a trace of caprolactam 1 was formed but with a 49% yield of adipamide 7.

A time course study of the reaction ranging from 0.5 to 4 hr (entries 13-17) was conducted; the best yield of caprolactam 1 (40%) was observed using a 1 hr reaction time (entry 14). Three or more hours of reaction time provided no detectable amount of caprolactam 1 (entries 16 and 17).

The conversion of trans,trans-MCA 4c to caprolactam 1 was also carried out using Pd/Silica (8.6% Pd/Davisil635) catalyst under standard hydrogenation conditions (entries 19-20). These conditions provided approximately the same yields of caprolactam 1 as observed with the copper chromite ($2CuO-Cr_2O_3$) catalyst.

Example 2

Conversion of cis,cis-muconamide 4a and cis,trans-muconamide 4b to Caprolactam 1 Over 8.6% Pd/Davisil635 Catalyst cis,cis-MCA 4a and cis,trans-MCA 4b were individually subjected to a series of reaction conditions in the manner previously described with trans,trans-MCA 4c. The results are summarized in Table 2 below. In the reaction series with cis,trans-MCA 4b (entries 1-3) the reaction was run using diglyme or dioxane as a solvent for 1 h to 1.5 h, and yields of about 30% of caprolactam 1 and about 30% of adipamide 7 were observed together with a trace amount of HMDA 8.

cis,cis-MCA 4a was also converted to caprolactam 1, (Table 2, entry 4), but with a relatively low yield of caprolactam 1 (6.2%), a 67% yield of adipamide 7 and no detectable amount of HMDA 8 or HMI 9.

Although all isomers of Q,Q-MCA were useful in making the desired caprolactam product, the order of preference of the isomers is trans,trans-MCA 4c>cis,trans-MCA 4b>cis, cis-MCA 4a under these reaction conditions.

Below are exemplary descriptions of individual reaction conditions listed in Table 1 and Table 2, which follow later.

Example 3

Preparation of Caprolactam 1 from trans,trans-muconamide 4c Using Copper Chromite/Zeolite Catalyst (Table 1, Entry 5)

Into a pressure reactor fitted with a glass-liner, trans,trans-MCA 4c (1 g, 7.1 mmol), copper chromite (0.5 g, 1.6 mmol, 22 mol %) and zeolite (1 g) were suspended in THF (100 mL). The sealed reaction vessel was purged with nitrogen (3×) and charged with anhydrous ammonia (50 psi) and then with $H_2$ (1600 psi) at RT. The Parr reactor was then heated and maintained at 250° C. for 2 hr. The reaction mixture was then allowed to cool to RT and the catalyst along with all insoluble material was removed by filtering the reaction mixture through a Whatman #2 Filter paper. The filtrate (100 mL) was analyzed by GCMS, which indicated a yield of caprolactam 1 (33%) and HMDA 8 (5%).

The desired product, caprolactam 1, was isolated by bulb-to-bulb distillation under reduced pressure (2 mmHg) using Kugelrohr apparatus; the NMR data matched with that of an authentic sample of caprolactam obtain from Aldrich.

Example 4

Preparation of Caprolactam 1 from cis,trans-muconamide 4b (Table 2, Entry 1)

Into a pressure reactor fitted with a glass-liner, cis,trans-MCA 4b (0.5 g, 3.6 mmol), 8.6% Pd/Davisil.635 (0.5 g, 5.6 mol %) were suspended in diglyme (100 mL). The sealed reaction vessel was purged with nitrogen (3×) and charged with anhydrous ammonia (50 psi) and then with $H_2$ (1600 psi) at RT. The pressure reactor was heated and maintained at 250° C. for 1 hr. The reaction mixture was then allowed to cool to RT and the catalyst was removed by filtering the reaction mixture through a Whatman #2 Filter paper. The filtrate was analyzed by GCMS, which indicated a yield of 34% caprolactam 1, 27% adipamide 7 and a trace amount of HMDA 8.

Example 5

Preparation of Caprolactam 1 from cis,cis-muconamide 4a (Table 2, Entry 4)

Into a pressure reactor fitted with a glass-liner, cis,cis-MCA 4a (0.5 g, 3.6 mmol), 8.6% Pd/Davisil.635 (0.5 g, 5.6 mol %) were suspended in THF (100 mL). The sealed reaction vessel was purged with nitrogen (3×) and charged with anhydrous ammonia (50 psi) and then with $H_2$ (1000 psi) at RT. The pressure reactor was heated and maintained at 250° C. for 3 hr. The reaction mixture was then allowed to cool to RT and the catalyst was removed by filtering the reaction mixture through a Whatman #2 Filter paper. The filtrate was analyzed by GCMS, which indicated a yield of 6% caprolactam 1 and 67% of adipamide 7; no HMDA or HMI were detected.

Example 6

Conversion of Adipamide 7 to Caprolactam 1 over 8.6% Pd/Davisil635 Catalyst

Adipamide may be formed by the hydrogenation of muconamide, and is a presumed intermediate in the reaction of muconamide to caprolactam. It is also possible to form adipamide via the treatment of adiponitrile or mucononitrile as described in a related application, filed concurrently with the present application, entitled "Process for Preparing Hexamethylenediamine and Polyamides Therefrom", filed on Apr. 9, 2012, which is incorporated by reference herein in its entirety, wherein various processes are described to make hexamethylenediamine. It is also possible to form adipamide via amidification of adipic acid. Adipic acid may be formed by hydrogenating one or more of Q,Q-MA, e.g., as described in U.S. Pat. No. 5,487,987, which is incorporated herein by reference in its entirety. Thus a series of reactions were performed in the same manner as described in Example 1 above, but using adipamide as the starting material. The results are collected in Table 3. In this series of reactions, the presence of hexamethyleneimine 9 (HMI) was detected along with the caprolactam product.

TABLE 1

| Entry | Catalyst type | Catalyst g | Zeolite g | Solvent | Temp °C. | Time hr | Pressure (psi) $H_2$ | Pressure (psi) $NH_3$ | Pressure (psi) Final | Results (% yield) HMDA | Results (% yield) CL | Results (% yield) adipamide |
|---|---|---|---|---|---|---|---|---|---|---|---|---|
| 1 | C | 0.1 | — | THF | 300 | 6 | 200 | 0 | 1650 | ND | ND | NA |
| 2 | C | 0.5 | 0.5 | THF | 200 | 6 | 300 | 0 | 1750 | ND | ND | 85 |
| 3 | C | 0.5 | 0.5 | THF | 300 | 6 | 300 | 0 | 1800 | ND | ND | 87 |
| 4 | C | 0.5 | 1 | THF | 250 | 3 | 1600 | 0 | 3000 | ND | <1 | NA |
| 5 | C | 0.5 | 1 | THF | 250 | 2 | 1600 | 50 | 3120 | 5.0 | 33 | NA |
| 6 | C | 0.5 | 1 | TBME | 250 | 3 | 1600 | 50 | 3105 | ND | <1 | NA |
| 7 | C | 0.11 | — | THF | 250 | 2 | 1725 | 50 | 3015 | ND | 5.4 | 33 |
| 8 | C | 0.22 | — | THF | 250 | 2 | 1715 | 50 | 2945 | ND | 13.3 | 30 |
| 9 | C | 1.0 | — | THF | 250 | 2 | 1680 | 50 | 3015 | 7.3 | <1 | 0 |
| 10 | C | 2.2 | — | THF | 250 | 2 | 1665 | 50 | 2950 | 6.7 | <1 | 0 |
| 11 | C | 0.5 | — | THF | 150 | 2 | 1680 | 50 | 3110 | ND | <1 | 76 |
| 12 | C | 0.5 | — | THF | 250 | 2 | 500 | 50 | 3110 | ND | <1 | 49 |
| 13 | C | 0.5 | — | THF | 250 | 0.5 | 1600 | 50 | 2600 | 4.9 | 18 | 53 |
| 14 | C | 0.5 | — | THF | 250 | 1 | 1600 | 50 | 2600 | 6.4 | 40 | 25 |
| 15 | C | 0.5 | — | THF | 250 | 2 | 1600 | 50 | 2600 | 8.2 | 27 | 26 |
| 16 | C | 0.5 | — | THF | 250 | 3 | 1600 | 50 | 2600 | 8.1 | 0 | 25 |
| 17 | C | 0.5 | — | THF | 250 | 4 | 1600 | 50 | 2600 | 7.6 | 0 | 18 |
| 18 | C | 0.5 | — | Dioxane | 250 | 1 | 1600 | 50 | 2600 | 9.1 | 25 | 38 |
| 19 | P | 0.5 | — | Dioxane | 250 | 1 | 1600 | 50 | 2600 | 6.1 | 22 | 28 |
| 20 | P | 0.5 | — | Diglyme | 250 | 1 | 1600 | 50 | 2600 | 6.0 | 28 | 30 |

C = copper chromite ($2CuO—Cr_2O_3$); P = 8.6% Pd/Davisil635; HMDA = hexamethylenediamine 8; CL = caprolactam 1; ND = not detected by GCMS; NA = not analyzed; TBME = t-butyl methyl ether.

TABLE 2

| Entry | Substrate Name | Substrate g | Catalyst (g) | Solvent | Pressure (psi) $H_2$ | Pressure (psi) $NH_3$ | Pressure (psi) Final[a] | Temp (°C.) | RPM | Time (h) | Results (% yield) HMDA | Results (% yield) CL | Results (% yield) Adipamide |
|---|---|---|---|---|---|---|---|---|---|---|---|---|---|
| 1 | ct-MCA | 1.0 | 0.5 | Diglyme | 1600 | 50 | 2600 | 250 | 600 | 1 | 0.07 | 34 | 27 |
| 2 | ct-MCA | 1.0 | 0.5 | Dioxane | 1600 | 50 | 2600 | 250 | 600 | 1 | 0.06 | 28 | 28 |
| 3 | ct-MCA | 1.0 | 0.5 | Diglyme | 1600 | 50 | 2600 | 250 | 600 | 1.5 | Trace | 26 | 39 |
| 4 | cc-MCA | 0.5 | 0.5 | THF | 1000 | 50 | 1750 | 250 | 600 | 3 | ND | 6.2 | 67 |

[a] = pressure at the end of the reaction before cooling the reactor.
ct-MCA = cis,trans-muconamide 4b; cc-MCA = cis,cis-muconamide 4a; HMDA = hexamethylenediamine 8; CL = caprolactam 1; ND = not detected

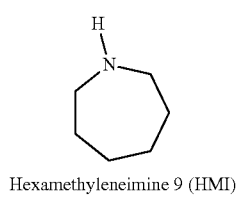

Hexamethyleneimine 9 (HMI)

Below is an exemplary description of one of the reaction conditions listed in Table 3.

Example 7

Preparation of Caprolactam 1 from Adipamide 7 (Table 3, Entry 1)

Into a pressure reactor fitted with a glass-liner, adipamide 7 (1.0 g, 6.94 mmol), 8.6% Pd/Davisil635 (0.5 g, 5.6 mol %) were suspended in diglyme (100 mL). The sealed reaction vessel was purged with nitrogen (3×) and charged with anhydrous ammonia (50 psi) and then with $H_2$ (1600 psi) to give a total pressure of 1650 psi at RT. The pressure reactor was heated and maintained at 250° C. for 2 hr. The reaction mixture was then cooled to RT and the catalyst was removed by filtering the reaction mixture through a Whatman #2 Filter paper. The filtrate was analyzed by GCMS, which indicated a 35% yield of caprolactam 1, a 28% yield of HMI 9, with 17% of adipamide 7 remaining unreacted.

TABLE 3

| | Substrate | | Catalyst | | Pressure (psi) | | | Temp | | Time | Results (% yield) | | | |
|---|---|---|---|---|---|---|---|---|---|---|---|---|---|---|
| Entry | Name | g | (g) | Solvent | $H_2$ | $NH_3$ | Final[a] | (° C.) | RPM | (h) | HMI | HMDA | CL | Adipamide |
| 1 | adipamide | 1.0 | 0.5 | Diglyme | 1600 | 50 | 2650 | 250 | 600 | 2.0 | 28 | Trace | 35 | 17 |
| 2 | adipamide | 1.0 | 1.0 | Diglyme | 1720 | 50 | 2760 | 250 | 600 | 2.5 | 42 | Trace | 21 | 2 |
| 3[b] | adipamide | 1.0 | 0.5 | Diglyme | 1000 | 50 | 1680 | 250 | 600 | 1 | 7.7 | Trace | 14 | 50 |
| 4 | adipamide | 1.0 | 0.5 | Diglyme | 500 | 50 | 1020 | 250 | 500 | 4.5 | 15 | Trace | 22 | 13 |
| 5 | adipamide | 1.0 | 0.5 | Diglyme | 1600 | 50 | 2650 | 250 | 500 | 1 | 7 | Trace | 12 | 50 |

[a] = pressure at the end of the reaction before cooling the reactor.
[b] = water added
HMDA = hexamethylenediamine 8; CL = caprolactam 1; HMI = Hexamethyleneimine 9

As it would be advantageous to produce caprolactam 1 from muconic acid without the need to synthesize muconamide or adipamide in a separate step, the direct reaction of the three double-bond isomers of muconic acid Q,Q-MA 3a-3c to caprolactam 1 was investigated and various combinations of ranges of the different reaction parameters were surveyed, that is, catalyst type and combination, reaction solvent, reactant concentration and catalyst loading, pressure of $NH_3$ and $H_2$, reaction temperature, and the different isomers of muconic acid. The cis,cis-isomer of muconic acid 3a was prepared by fermentation of sugars from renewable biomass as described, for example, in U.S. Pat. Nos. 4,879,987 and 5,487,987, and the cis,trans- and trans,trans-isomers 3b and 3c were prepared from cis,cis-isomer of muconic acid 3a as described in Starting Material Examples A and B respectively.

Example 8

Preparation of Caprolactam 1 Directly from Muconic Acid [Q,Q-MA 3a-3c]

The results of the different individual reactions from the survey of the various reaction parameters are listed in Tables 4A through 4G below, each table summarizing the results of varying a particular reaction variable or combination of variables as indicated in each table. Unless otherwise indicated, the reaction conditions used were: the trans,trans-MA isomer 3c at a 70 mM concentration, 500 psi $H_2$, 50 psi $NH_3$, dioxane, with 5% Pd/$Al_2O_3$ (5 mol %, calculated as mols of Pd vs. mols of trans,trans-MA 3c) for 2 hr. Reactions were run in a pressure reactor (Model 4575/76 HP/HT from the Parr Instrument Company), with a 100 mL total reaction volume.

Catalyst Type (Table 4A)

In Table 4A, entries 1-11 are heterogeneous catalysts; entries 12-15 are homogeneous catalysts. Pd(acac)$_2$ was purchased from Strem; Pd/Davisil 635 is made at the time of use; and the other catalysts were purchased from Sigma-Aldrich or Johnson-Matthey.

TABLE 4A

| | | Catalyst Type[a] | | | |
|---|---|---|---|---|---|
| Entry | Substrate | Catalyst | CL yield (% by HPLC)[e] | HMI yield (% by HPLC)[e] | Adipamide yield (% by HPLC)[e] |
| 1[b] | tt-MA | 8.6% Pd/Davisil 635 | 30% | 5% | 55% |
| 2[b] | tt-MA | 10% Pd/C | 23% | 4% | 38% |
| 3 | tt-MA | 5% Pd/$Al_2O_3$ | 44% | 6% | 38% |
| 3bis[c] | tt-MA | 5% Pd/$Al_2O_3$ | 31% | NA | 53% |
| 4 | tt-MA | 10% Pd/$Al_2O_3$ | 38% | 3% | 50% |

TABLE 4A-continued

| | | Catalyst Type[a] | | | |
|---|---|---|---|---|---|
| Entry | Substrate | Catalyst | CL yield (% by HPLC)[e] | HMI yield (% by HPLC)[e] | Adipamide yield (% by HPLC)[e] |
| 5 | tt-MA | 5% Ru/$Al_2O_3$ | 4% | ND | ND |
| 5bis[c] | tt-MA | 5% Ru/$Al_2O_3$ | 58% | 12% | ND |
| 6[d] | tt-MA | 5% Pt/$Al_2O_3$ | 39% | 40% | ND |
| 7 | tt-MA | 5% Pt/C | 47% | 14% | 8% |
| 8 | tt-MA | 5% Rh/$Al_2O_3$ | 56% | 6% | 14% |
| 8bis[c] | tt-MA | 5% Rh/$Al_2O_3$ | 43% | 6% | 28% |
| 9 | tt-MA | 5% Rh/C | 58% | 13% | 13% |
| 10 | tt-MA | 2CuO•$Cr_2O_3$ | ND | ND | ND |
| 11 | tt-MA | 65% Ni/Si $Al_2O_3$ | ND | ND | 30% |
| 12 | tt-MA | Ru(acac)$_3$/TRIPHOS | 38% | ND | 20% |

TABLE 4A-continued

| Entry | Substrate | Catalyst | CL yield (% by HPLC)[e] | HMI yield (% by HPLC)[e] | Adipamide yield (% by HPLC)[e] |
|---|---|---|---|---|---|
| 13 | tt-MA | Pd(acac)$_2$ | 5% | ND | 58% |
| 14 | tt-MA | Pd(acac)$_2$/TRIPHOS | ND | ND | ND |
| 15 | tt-MA | Pd(acac)$_2$/PPh$_3$ | ND | ND | ND |

[a] = Catalyst (5 mol %), H$_2$ (500 psi), NH$_3$ (saturated to 50 psi), dioxane, 250° C. (pressure at 250° C., 1300 psi), 2 h;
[b] = H$_2$ (2000 psi);
[c] = 5% Pd/Al$_2$O$_3$ #12 Johnson Matthey (1 mol %); 5% Ru/Al$_2$O$_3$ #39 Johnson Matthey (1 mol %); 5% Rh/Al$_2$O$_3$ #36 Johnson Matthey (1 mol %).
[d] = H$_2$ (1000 psi);
[e] = ND: not detected.

Catalyst Combinations (Table 4B)

The use of combined catalysts was surveyed. 5% Ru/Al$_2$O$_3$ #39 in combination with 5% Pd/Al$_2$O$_3$ #13 (0.7 mol % and 0.33 mol %, respectively) offered the best yield of caprolactam.

TABLE 4B

Combined Catalysts[a]

| Entry | Catalyst JM# | H$_2$ press. | CL yield (% by HPLC) | HMI yield (% by HPLC)[b] | Adipamide yield (% by HPLC) |
|---|---|---|---|---|---|
| 1 | 5% Ru/Al$_2$O$_3$ #39 (1.05 mol %) | 200 psi | 6% | ND | 47% |
| 2 | 5% Pd/Al$_2$O$_3$ #12 (1.0 mol %) | 200 psi | 26% | NA | 68% |
| 3 | 5% Ru/Al$_2$O$_3$ #39 (0.5 mol %) 5% Pd/Al$_2$O$_3$ #12 (0.5 mol %) | 200 psi | 32% | 4% | 45% |
| 4 | 5% Ru/Al$_2$O$_3$ #39 (0.7 mol %) 5% Pd/Al$_2$O$_3$ #12 (0.33 mol %) | 200 psi | 19% | 1% | 64% |
| 5 | 5% Ru/Al$_2$O$_3$ #39 (0.7 mol %) 5% Pd/Al$_2$O$_3$ #13 (0.33 mol %) | 300 psi | 59% | 12% | 10% |
| 6 | 5% Ru/Al$_2$O$_3$ #39 (0.7 mol %) 5% Pd/C #5 (0.22 mol %) | 200 psi | 39% | 3% | 43% |
| 7 | 5% Ru/Al$_2$O$_3$ #39 (0.52 mol %) 5% Pt/Al$_2$O$_3$ #32 (0.27 mol %) | 200 psi | 12% | ND | 73% |

[a] = tt-MA 3c concentration was 70 mM, NH$_3$ (saturated to 50 psi), dioxane, 250° C., 2 h;
[b] = ND: not detected.
NA = not analyzed

Reaction Solvent (Table 4C)

Dioxane and diglyme gave comparable results.

TABLE 4C

Solvent Study[a]

| Entry | Solvent Concentration | Temp (° C.) Time | Initial H$_2$ pressure (max press.) | NH$_3$ source and quantity | CL yield (% by GC)[c] | HMI yield (% by GC)[c] | Adipamide yield (% by HPLC)[c] |
|---|---|---|---|---|---|---|---|
| 1 | Dioxane | 250 2 h | 2000 psi (3300 psi) | Gas NH$_3$ 60 psi (3 times) | 30% | 5% | 55% |
| 2 | Dioxane/H$_2$O 95/5 | 250 12 h | 2000 psi (3590 psi) | Gas NH$_3$ 50 psi (saturated) | 35% | 6% | 42% |
| 3 | Dioxane/H$_2$O 95/5 | 250 24 h | 2000 psi (3630 psi) | Gas NH$_3$ 50 psi (saturated) | 41% | 34% | 28% |
| 4 | Dioxane/MeOH 95/5 | 250 2 h | 500 psi (1320 psi) | Gas NH$_3$ 50 psi (saturated) | 11% | ND | 40% |
| 5[b] | DMSO | 250 2 h | 500 psi (2080 psi) | liquid NH$_3$ (5.75 g) | ND | ND | ND |
| 6 | Diglyme | 250 2 h | 2000 psi (3300 psi) | Gas NH$_3$ 60 psi (3 times) | 33% | 19% | ND |

[a] = tt-MA, 8.6% Pd/Davisil 635 (5 mol %), 250° C.;
[b] = 5% Pd/Al$_2$O$_3$ Sigma Aldrich (5 mol %);
[c] = ND: not detected;
[d] = tt-MA 3c concentration was 70 mM in all reactions Concentration and Catalyst Loading (Table 4D)

The best results were obtained with 15 wt % catalyst (e.g. 150 mgs total catalyst mass per 1.0 g of muconic acid, as in Table 4D, entry 1).

TABLE 4D

Catalyst Loading and MA Concentration[a]

| Entry | Catalyst (JM#) | $H_2$ (psi) | Muconic Acid Concentration | CL (% by HPLC) | HMI (% by HPLC)[b] | Adipamide (% by HPLC) |
|---|---|---|---|---|---|---|
| 1 | 5% Ru/Al$_2$O$_3$ #39 (0.7 mole %) 5% Pd/Al$_2$O$_3$ #13 (0.33 mol %) | 300 | 0.07M | 59% | 12% | 10% |
| 2 | 5% Ru/Al$_2$O$_3$ #39 (0.53 mol %) 5% Pd/Al$_2$O$_3$ #13 (0.17 mol %) | 200 | 0.07M | 23% | ND | 64% |
| 3 | 5% Ru/Al$_2$O$_3$ #39 (0.7 mol %) 5% Pd/Al$_2$O$_3$ #13 (0.33 mol %) | 200 | 0.35M | 23% | 2% | 52% |
| 4 | 5% Ru/Al$_2$O$_3$ #39 (0.7 mol %) 5% Pd/Al$_2$O$_3$ #13 (0.33 mol %) | 700 | 0.35M | 51% | 13% | ND |

[a] = tt-MA, NH$_3$ (saturated to 50 psi), dioxane, 250° C., 2 h
[b] = ND: Not detected Hydrogen Pressure (Table 4E)

H$_2$ pressure between 200-2000 psi gave comparable results (Table 4E, entries 1-4).

TABLE 4E

H$_2$ Pressure Study[a]

| Entry | Catalyst | Initial H$_2$ pressure (max press.) | CL yield (% by GC) | HMI yield (% by GC)[b] | Adipamide yield (% by HPLC)[b] |
|---|---|---|---|---|---|
| 1 | 8.6% Pd/Davisil635 | 2000 psi (3300 psi) | 30% | 5% | 55% |
| 2 | 8.6% Pd/Davisil635 | 500 psi (1300 psi) | 27% | 4% | 47% |
| 3 | 5% Pd/Al$_2$O$_3$ | 520 psi (1350 psi) | 44% | 6% | 28% |
| 4 | 5% Pd/Al$_2$O$_3$ | 200 psi (880 psi) | 46% | 7% | 28% |
| 5 | 5% Pd/Al$_2$O$_3$ | 100 psi (850 psi) | 26% | ND | 52% |

[a] = Catalyst (5 mol %), tt-MA, NH$_3$ (saturated to 50 psi), dioxane (0.07M), 250° C., 2 h; and
[b] = ND: not detected.

Reaction Temperature (Table 4F)

Temperatures higher than 200° C., when using 5% Pd/Al$_2$O$_3$, gave higher caprolactam yield.

TABLE 4F

Temperature Study[a]

| Entry | Catalyst | Temp (° C.) Rxn. Time | CL yield (% by GC) | HMI yield (% by GC)[b] | Adipamide yield (% by HPLC) |
|---|---|---|---|---|---|
| 1 | 5% Pd/Al$_2$O$_3$ | 250 2 hr | 44% | 6% | 28% |
| 2 | 5% Pd/Al$_2$O$_3$ | 280 1 hr | 55% | 15% | 11% |
| 3 | 5% Pd/Al$_2$O$_3$ | 200 2 hr | 7% | ND | 64% |

[a] = tt-MA, catalyst (5 mol %), H$_2$ (500 psi), NH$_3$ (saturated to 50 psi), dioxane (0.07M); and
[b] = ND: not detected.

Muconic Acid Isomer (Table 4G)

cis,cis-MA 3a and cis,trans-MA 3b gave comparable results, while the trans,trans-MA 3c appears to be less reactive.

TABLE 4G

Variation in Muconic Acid Isomer[a]

| Entry | Substrate | Catalyst | CL yield (% by GC) | HMI yield (% by GC)[b] | Adipamide yield (% by HPLC)[c] |
|---|---|---|---|---|---|
| 1 | cc-MA | 5% Pd/Al$_2$O$_3$ | 55% | 13% | 9% |
| 2 | ct-MA | 5% Pd/Al$_2$O$_3$ | 54% | 7% | 18% |
| 3 | tt-MA | 5% Pd/Al$_2$O$_3$ | 44% | 6% | 28% |

[a] = Catalyst (5 mol %), H$_2$ (500 psi), NH$_3$ (saturated to 50 psi), dioxane (0.07M), 250° C. (pressure at 250° C., 1300 psi), 2 hr
[b] = NA: not analyzed
[c] = ND: not detected Example 9

Preparation of Caprolactam 1 from trans,trans-muconic Acid 3c

5% Ru/Al$_2$O$_3$ (0.5 g, 0.25 mmol, 0.7 mol %) and 5% Pd/Al$_2$O$_3$ (0.25 g, 0.12 mmol, 0.33 mol %) was added to trans,trans-MA 3c (4.97 g, 35 mmol, 1 eq.) in 1,4-dioxane (0.1 L, 0.35 M), and the suspension charged to a pressure reactor. The reactor was sealed and purged with $N_2$ (3×) then with $NH_3$ (3×). The reactor was filled with $NH_3$ and the contents stirred for 15 minutes with the input of $NH_3$ continuing until the pressure stabilized at 50 psi. To this mixture was added 700 psi of $H_2$ to give a total pressure of 750 psi in the reactor. The reaction was heated and maintained at 250° C. for 2 hr.

HPLC analysis of the crude mixture diluted in water indicated caprolactam 1 (51%), HMI 9 (13%), and adipamide 7 (3%).

In the course of preparing muconic acid via fermentation of sugars from renewable biomass, the production of one or more of the isomers of muconolactone 5 can occur. It is advantageous to make use of this material to prepare caprolactam 1 without separation of the individual double-bond isomers.

Example 10

Preparation of Caprolactam 1 from Muconolactone 5 Using Palladium Catalyst

5% $Pd/Al_2O_3$ (0.742 g, 0.35 mol, 5 mol %) was added to muconolactone 5 (0.987 g, 7 mmol, 1 eq.) in 1,4-dioxane (100 mL, 0.07 M). The suspension was placed into a pressure reactor. The sealed apparatus was purged with $N_2$ (3×) then with $NH_3$ (3×). The reactor was filled with $NH_3$ and maintaining an input of $NH_3$ over 5 min, the pressure stabilized at 50 psi. This was added 600 psi of $H_2$ to give a total pressure of 650 psi in the reactor. The reaction was heated and maintained at 250° C. for 2 hr.

After cooling to RT, the reaction mixture was dissolved in water and analyzed by HPLC. A 43% yield of caprolactam 1 was achieved, with no detected formation of adipamide 7.

Example 11

Preparation of Caprolactam 1 from Muconolactone 5 Using a Ruthenium and Palladium Catalyst 5% $Ru/Al_2O_3$ (0.1 g, 0.05 mmol, 0.7 mol %) and 5% $Pd/Al_2O_3$ (0.05 g, 0.023 mmol, 0.33 mol %) is added to muconolactone (0.994 g, 7 mmol, 1 eq.) in 1,4-dioxane (0.1 L, 0.07 M, 1 wt %), and the suspension is charged into a pressure reactor. The reactor is sealed and purged with $N_2$ (3×) and with $NH_3$ (3×). The reactor is then filled with $NH_3$ and the pressure is allowed to stabilize at 50 psi. $H_2$ is then added to give a total pressure of 650 psi in the reactor. The reaction is heated to 250° C. for 2 hr.

Example 12

Preparation of Caprolactam 1 from Muconamide [Q,Q-MCA 3a-3c] Using a Ruthenium and Palladium Catalyst 5% $Ru/Al_2O_3$ (0.1 g, 0.05 mmol, 0.7 mol %) and 5% $Pd/Al_2O_3$ (0.05 g, 0.023 mmol, 0.33 mol %) is added to Q,Q-MCA (1.0 g, 7 mmol, 1 eq.) in 1,4-dioxane (0.1 L, 0.07 M, 1 wt %) and the suspension is charged into a pressure reactor. The reactor is sealed and purged with $N_2$ (3×) and with $NH_3$ (3×). The reactor is then filled with $NH_3$ and the pressure is allowed to stabilize at 50 psi. $H_2$ is then added to give a total pressure of 650 psi in the reactor. The reaction is heated to 250° C. for 2 hr.

It is highly advantageous to prepare caprolactam 1 by treating fermentation broth that contains one or more of the isomers of muconic acid made by the fermentation of sugars form renewable bio-based feedstock without having to first isolate the muconic acid. The avoidance of the separation step gives a simpler overall process for the production of caprolactam which requires less equipment and time to perform.

Example 13

Preparation of Caprolactam 1 from Muconic Acid [Q,Q-MA 3a-3c] in Fermentation Broth Fermentation broth containing one or more isomers of muconic acid Q,Q-MA 3a-3c, and optionally, one or more of the double-bond isomers of muconolactone 5, is filtered to remove cells, cell debris and proteins in the manner described in PCT Patent Application No. PCT/US2011/020681, filed Jan. 10, 2011. This fermentation broth may be concentrated to give a convenient concentration of Q,Q-MA 3a-3c as may be desired.

The fermentation broth is then mixed with 1,4-dioxane and the catalysts 5% $Ru/Al_2O_3$ (0.1 g, 0.05 mmol, 0.7 mol %) and 5% $Pd/Al_2O_3$ (0.05 g, 0.023 mmol, 0.33 mol %) are added, and the suspension is charged into a pressure reactor. The reactor is sealed and purged with $N_2$ (3×) and with $NH_3$ (3×). The reactor is then filled with $NH_3$ and the pressure is allowed to stabilize at 50 psi. $H_2$ is then added to give a total pressure of 650 psi in the reactor. The reaction is heated to 250° C. for 2 hr.

Example 14

Preparation of Caprolactam 1 from Muconic Acid Via Route 5 (Hydrogenation of Muconic Acid to Adipic Acid 10, Conversion of Adipic Acid to Caprolactam 1)

Adipic acid 10 is obtained by hydrogenating one or more of Q,Q-MA 3a-3c in a batch reactor or in a flow reactor. A typical protocol for a batch reaction is as follows. 5% Pd/C (E 101 R/W catalyst available from Evonik) (catalyst loading is 14 wt % based on cis,cis-MA, 54.5 wt % moisture) is added to a suspension of microbially-obtained cis,cis-MA in THF (23 wt %) placed in a Parr reactor. The system is sealed and purged three times with nitrogen. The system is equipped with a cooling system that is set to control temperature at 60° C. The reactor is stirred at 600 rpm or higher. Hydrogen is added as a continuous pressure of 700 psig for 4-5 h. The reactor is vented safely, and the reaction mixture is diluted to solubilize adipic acid (about 9 wt %). The mixture is stirred for 1 h and filtered through a Celite bed. The solvent is evaporated to afford a white solid at 95% yield or higher. In some cases, the adipic acid is yellow and is recrystallized by preparing a 21 wt % suspension of adipic acid and heating to 80° C. and subsequently filtering. The filtrate is allowed to cool overnight in a refrigerator. Adipic acid is recovered by filtration. A typical protocol for a flow reaction is as follows. cis,cis-MA is dissolved in THF at 5 wt %. The solution is hydrogenated in a trickle bed reactor at 500 psig and 130° C. with a pre-reduced nickel catalyst (e.g., $Ni/Al_2O_3$—$SiO_2$ catalyst such as NISAT® RS-300, available from Sud-Chemie). A feed preheater is used to heat the center of the bed to 130° C. The adipic acid solution is cooled and concentrated to afford adipic acid. The batch hydrogenation or flow hydrogenation may be carried out for cis,trans-MA or trans,trans-MA.

Adipic acid is reacted with ammonia to form the diammonium salt, which is heated to form adipamide, which is catalytically reduced to form caprolactam. A suspension of adipic acid in THF (4.1 kg adipic acid/55 L THF, 0.41 kg 5% $Ru/Al_2O_3$, D302011-5, available from Johnson-Matthey) is charged to a reactor. The reaction mixture is stirred at 1500-2000 rpm. Following purging with nitrogen (3×), the reactor is purged (3×) and then charged with ammonia gas at room temperature to reach 60 psig to form the diammonium salt. After the ammonia pressure is stable, hydrogen is added to reach a total pressure of 860 psig. The reactor is heated to 250° C. over a period of 45-120 min. The pressure is 1800-2000 psi at 250° C. if reactor is used at half capacity. Optionally, the reactor may be heated before addition of hydrogen. After 80 min. at 250° C., the reactor is cooled. The mixture is cooled as quickly as possible to minimize formation of HMI, e.g., cooled from 250° C. to 150° C. in about 10 minutes. After the reactor is cooled to room temperature, gas is vented and the suspension filtered using a 6 micron membrane to remove catalyst. The filtrate is distilled at atmospheric pressure to remove THF (b.p.=66° C.) and HMI (b.p.=138° C.). The distillate is subjected to fractional distillation at 0.75-15 mm Hg vacuum at 120-150° C. The distillate is a colorless liquid that solidifies upon cooling. The solid is recrystallized in 2:1 v/v MTBE/hexanes (caprolactam m.p.=68-71° C.), repeated as necessary to yield 99.9% pure caprolactam by GC.

For reference, effect of temperature and time of catalytic reduction on reaction yield are studied using a 500 mL Parr reactor, 50 psi NH$_3$, dioxane (0.07M, 1 wt %) and 5 wt % 5% Pd/Al$_2$O$_3$ catalyst are studied using trans,trans-muconic acid as the substrate. The trans,trans-muconic acid is hydrogenated in situ by the catalyst to form adipic acid. Initial hydrogen pressure is 200 psi, so that the total initial pressure after charging with hydrogen is 250 psi. Results are shown in Table 5A. The time listed includes the beginning of heating a room temperature to the time at which the reaction is cooled down. The temperature ramp time from room temperature to 250° C. is 45-60 min. At 225° C. (entry 3), adipamide is the main product as hydrogenation is relatively slow at this temperature. Also observed is the presence of monoamide, showing amidification is not complete. Increasing reaction temperature to 250° C. (entry 1) results in complete amidification and increases rate of hydrogenation of adipamide to an intermediate 6-aminohexanamide which cyclizes to form caprolactam. Increasing reaction time to 3 h (entry 2) results in complete reduction of the adipamide but also increases the reduction of caprolactam to HMI. The reaction is heated to 250° C. for a time that allows formation of caprolactam without undesired production of HMI. ND=not detected. t,t-MA=trans,trans-muconic acid.

TABLE 5A

| Entry | Substrate | Temp., Time | H$_2$ pres. | CL yield (% by HPLC) | HMI yield (% by HPLC) | Adipamide yield (% by HPLC) | Other peaks | % Mol balance |
|---|---|---|---|---|---|---|---|---|
| 1 | t,t-MA | 250° C., 2 h | 200 psi | 41% | 5% | 40% | | 86 |
| 2 | t,t-MA | 250° C., 3 h | 200 psi | 59% | 15% | ND | Some hexanamide | 74 |
| 3 | t,t-MA | 225° C., 2 h | 200 psi | 11% | ND | 69% | Some monoamide 28% | 108 |

Increasing the adipic acid loading requires increasing the hydrogen pressure for desired conversion to caprolactam. Effect of substrate loading, H$_2$ pressure, and reaction time are shown in Table 5B. Reactions are run with NH$_3$ gas (saturated to 60 psi) at 250° C., in THF, with adipic acid derived from microbial muconic acid as the starting material. The reaction time includes the temperature ramp from room temperature to 250° C. of about 40 minutes. The catalyst used is 5% Ru/Al$_2$O$_3$ as described above in the typical protocol for making caprolactam from adipic acid (10 wt % loading based on substrate). Entry (6) shows a representative set of conditions that may provide an optimum balance of adipic acid loading, caprolactam yield and mol balance. AD=adipamide, VL=valeramide, HX=hexanamide.

TABLE 5B

| Entry | Conc (wt %) | H$_2$ (psig) | P at 250° C. (psig) | Time (h) | CL yield (mol %) | HMI yield (mol %) | AD yield (mol %) | VL yield (mol %) | HX yield (mol %) | Mol balance (%) |
|---|---|---|---|---|---|---|---|---|---|---|
| 1 | 5 | 750 | ND | 3 | 50 | 9 | 0 | 2 | 2 | 63 |
| 2 | 5 | 635 | ND | 2 | 34 | 1 | 2 | 0 | 0 | 37 |
| 3 | 5 | 1000 | 2633 | 1.75 | 53 | 4 | 2 | 2 | 1 | 62 |
| 4 | 5 | 1000 | 2267 | 1.5 | 49 | 4 | 2 | 2 | 1 | 57 |
| 5 | 5 | 1000 | 3000 | 2 | 64 | 6 | 2 | 2 | 4 | 78 |
| 6 | 7.5 | 863 | ND | 2 | 50 | 3 | 3 | 1 | 1 | 58 |
| 7 | 7.5 | 1000 | ND | 2 | 47 | 5 | 2 | 2 | 1 | 57 |
| 8 | 12.7 | 1375 | ND | 1.75 | 40 | 3 | 3 | 1 | 0 | 47 |
| 9 | 12.7 | 1318 | ND | 2 | 43 | 2 | 3 | 2 | 1 | 51 |
| 10 | 12.7 | 1480 | 2566 | 2.5 | 39 | 3 | 1 | 3 | 2 | 47 |
| 11 | 12.7 | 1450 | 2335 | 3 | 38 | 2 | 1 | 4 | 2 | 48 |
| 12 | 12.7 | 1430 | 2159 | 4 | 28 | 0 | 2 | 3 | 1 | 34 |

Under standard conditions (250° C., 2 h reaction time, ammonia pressure 50-60 psig, initial hydrogen pressure 200-2000 psig) caprolactam reacts to form HMI 9 and other products (e.g., valeramide 11 and hexanamide 12). Lowering the temperature reduces the loss of caprolactam to these other products. Adipamide and caprolactam are not observed at temperatures below 180-200° C., but caprolactam may react at temperatures above 160-180° C., so that the cooling rate to temperatures below 160° C. may influence reaction selectivity. After 2 h at 250° C. and initial 50-60 psig $NH_3$, 200 psig $H_2$, 40% of caprolactam is lost, whereas after 2 h at 200° C. (initial 50-60 psig $NH_3$, 200 psig $H_2$) 25% of caprolactam is lost. The main product formed at 200° C. is HMI and the main product formed at 250° C. is valeramide. At a loading of 5 wt % adipic acid in THF, 275 mL THF in a 500 mL reactor, 10 wt % loading (based on substrate) 5% $Ru/Al_2O_3$ as described for typical protocol for making caprolactam from adipic acid, and a total initial pressure of 780 psig (60 psig $NH_3$, 720 psig $H_2$), caprolactam concentration reaches a plateau at 60-65% after 130-150 minutes reaction time (80-100 minutes at 250° C.). Under these conditions, HMI concentration increases slowly after caprolactam starts to form. Adipamide is reduced to form caprolactam as the reaction progresses. The concentration of adipamide begins to decrease after 110 minutes and is low after 150 minutes. After about 150 minutes, caprolactam concentration begins to decrease due to reduction of caprolactam to form HMI.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

INCORPORATION BY REFERENCE

Reference is made to PCT International Patent Application entitled "Process for Preparing Hexamethylenediamine and Polyamides Therefrom", Attorney Docket No. 136556-013002/PCT, filed on Apr. 9, 2012, the entire content of which is hereby incorporated by reference in its entirety. All publications, patent applications and patents mentioned herein are hereby incorporated by reference in their entirety as if each individual publication, patent application and patent was specifically and individually indicated to be incorporated by reference.

The invention claimed is:

1. A process for preparing caprolactam of formula 1, comprising:

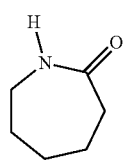

1 reacting one or more of cis, cis-, cis, trans- and trans,trans-muconic acid (Q,Q-MA), directly or after converting into an intermediate product, with ammonia and hydrogen, in the presence of a catalyst; and
forming caprolactam therefrom.

2. The process of claim 1, wherein the reacting step comprises reactions via Route 1:
converting Q,Q-MA to caprolactam in an aprotic polar solvent, using $H_2$ and $NH_3$ gases at a total initial pressure from about 250 to about 2050 psi, at a temperature from about 200 to about 300° C., and in the presence of at least one catalyst.

3. The process of claim 2, wherein the aprotic polar solvent is 1,4-dioxane, diglyme or DMSO.

4. The process of claim 2, wherein the aprotic polar solvent is mixed with water or an alcohol.

5. The process of claim 4, wherein the alcohol is MeOH.

6. The process of claim 2, wherein the at least one catalyst comprises one or more of Pd, Pt, Rh and Ru.

7. The process of claim 6, wherein the at least one catalyst comprises Ru and Pt or Ru and Pd.

8. The process of claim 2, wherein the at least one catalyst is present at from about 0.3 to about 1 mol %.

9. The process of claim 2, wherein the converting step takes about 0.5 to about 3 hours.

10. The process of claim 1, wherein the reacting step comprises reactions via Route 2:
(1) converting one or both of the cis,cis-MA and cis,trans-MA to one or both of $\Delta^\alpha$-muconolactone and $\Delta^\beta$-muconolactone; and
(2) reacting one or both of $\Delta^\alpha$-muconolactone and $\Delta^\beta$-muconolactone to form caprolactam, using $H_2$ and $NH_3$ gases, and in the presence of at least one catalyst.

11. The process of claim 10, wherein in Route 2, step (1) the converting is conducted by heating at reflux in aq. acetic acid.

12. The process of claim 11, wherein in Route 2, step (1) the aq. acetic acid is mixed with water at a ratio of about 1:2 acetic acid:water.

13. The process of claim 10, wherein in Route 2, step (2) the $H_2$ and $NH_3$ gases are provided at a total initial pressure from about 250 to about 650 psi.

14. The process of claim 10, wherein in Route 2, step (2) the reacting is conducted at a temperature from about 200 to about 300° C.

15. The process of claim 10, wherein in Route 2, step (2) the at least one catalyst comprises one or more of Pd, Pt, Rh and Ru.

16. The process of claim 15, wherein in Route 2, step (2) the at least one catalyst comprises Ru and Pd.

17. The process of claim 10, wherein in Route 2, step (2) the at least one catalyst is present at from about 0.5 to about 5 mol %.

18. The process of claim 10, wherein Route 2, step (2) takes about 0.5 to about 3 hours.

19. The process of claim 1, wherein the reacting step comprises reactions via Route 3:
(1) converting Q,Q-MA to one or more of cis,cis-, cis, trans- and trans,trans-muconate diester;
(2) converting one or more of cis,cis-, cis,trans- and trans, trans-muconate diester to one or more of cis,cis-, cis, trans- and trans,trans-muconamide (Q,Q-MCA) in aq. $NH_3$; and
(3) converting Q,Q-MCA to caprolactam in an aprotic polar solvent, using $H_2$ and $NH_3$ gases, and in the presence of a catalyst.

20. The process of claim 19, wherein in Route 3, step (1) the converting is conducted in aq. NaOH with dimethylsulfate.

21. The process of claim 20, wherein in Route 3, step (1) the converting is conducted at room temperature.

22. The process of claim 19, wherein Route 3, step (1) includes converting trans,trans-MA to trans,trans-muconic diester in methanol containing a catalytic amount of sulfuric acid while heating at reflux.

23. The process of claim 19, wherein in Route 3, step (2), the aq. $NH_3$ is mixed with an alcohol.

24. The process of claim 23, wherein the alcohol is MeOH or EtOH.

25. The process of claim 23, wherein a ratio of the aq. $NH_3$ to the alcohol is about 1:1.

26. The process of claim 19, wherein in Route 3, step (3) the aprotic polar solvent is THF, 1,4-dioxane or diglyme.

27. The process of claim 19, wherein in Route 3, step (3) the $H_2$ and $NH_3$ gases are provided at a total initial pressure from about 1000 to about 1600 psi.

28. The process of claim 19, wherein in Route 3, step (3) the converting is conducted at a temperature from about 200 to about 300° C.

29. The process of claim 19, wherein in Route 3, step (3) the catalyst comprises $2CuO$—$Cr_2O_3$ or Pd.

30. The process of claim 19, wherein in Route 3, step (3) the catalyst is present at from about 5 to about 50 mol %.

31. The process of claim 19, wherein Route 3, step (3) takes about 1 to about 3 hours.

32. The process of claim 19, wherein the muconic diester is dimethyl muconate.

33. The process of claim 1, wherein the reacting step comprises reactions via Route 4:
(1) converting Q,Q-MA to one or more of cis,cis-, cis, trans- and trans,trans-muconate diester;
(2) converting one or more of cis,cis-, cis,trans- and trans, trans-muconate diester to one or more of cis,cis-, cis, trans- and trans,trans-muconamide (Q,Q-MCA) in aq. $NH_3$;
(3) reducing the Q,Q-MCA to adipamide using $H_2$, in the presence of a first catalyst; and
(4) reducing the adipamide to yield caprolactam in an aprotic polar solvent, using $H_2$ and $NH_3$ gases, in the presence of a second catalyst.

34. The process of claim 33, wherein in Route 4, step (1) the converting is conducted in aq. NaOH with dimethylsulfate.

35. The process of claim 34, wherein in Route 4, step (1) the converting is conducted at room temperature.

36. The process of claim 33, wherein Route 4, step (1) includes converting trans,trans-MA to trans,trans-muconate diester in methanol containing a catalytic amount of sulfuric acid while heating at reflux.

37. The process of claim 33, wherein in Route 4, step (2), the aq. $NH_3$ is mixed with an alcohol.

38. The process of claim 37, wherein the alcohol is MeOH or EtOH.

39. The process of claim 37, wherein a ratio of the aq. $NH_3$ to the alcohol is about 1:1.

40. The process of claim 33, wherein in Route 4, step (3) the $H_2$ is provided at an initial pressure from about 300 to about 1600 psi.

41. The process of claim 33, wherein in Route 4, step (3) the first catalyst comprises $2CuO$—$Cr_2O_3$, Pd, Pt, Rh or Ru.

42. The process of claim 33, wherein in Route 4, step (3) the first catalyst is present from about 5 to about 25 mol %.

43. The process of claim 33, wherein in Route 4, step (3) the reducing is conducted at a temperature from about 200 to about 300° C.

44. The process of claim 33, wherein in Route 4, step (4) the aprotic polar solvent is diglyme.

45. The process of claim 33, wherein in Route 4, step (4) the $H_2$ and $NH_3$ gases are provided at a total initial pressure from about 500 to about 1650 psi.

46. The process of claim 33, wherein in Route 4, step (4) the second catalyst comprises one or more of Pd, Pt, Rh and Ru.

47. The process of claim 33, wherein in Route 4, step (4) the second catalyst is present from about 5 to about 10 mol %.

48. The process of claim 33, wherein in Route 4, step (4) the reducing is conducted at a temperature from about 200 to about 300° C.

49. The process of claim 33, wherein in Route 4, step (4) takes about 1 to about 3 hours.

50. The process of claim 33, wherein the muconic diester is dimethyl muconate.

51. A process for preparing nylon 6, comprising: polymerizing caprolactam, wherein the caprolactam is prepared according to the process of claim 1 from biomass-derived Q,Q-MA and contains a detectable amount of $^{14}C$ determined according to ASTM D6866.

52. The process of claim 51, wherein the caprolactam contains up to 0.0000000001% $^{14}C$.

53. A process for preparing a polyamide, comprising: reacting caprolactam with a compound having at least two amide-forming groups, wherein the caprolactam is prepared according to the process of claim 1 from biomass-derived Q,Q-MA and contains a detectable amount of $^{14}C$ determined according to ASTM D6866.

54. The process of claim 53, wherein the caprolactam contains up to 0.0000000001% $^{14}C$.

55. The process of claim 53, wherein the compound having at least two amide-forming groups comprises one or more of aliphatic or aromatic amino carboxylic acids, aliphatic or aromatic diamines, aliphatic or aromatic dicarboxylic acids, or salts or halides or esters thereof.

56. The process of claim 1, wherein the reacting step reactions via Route 5: converting Q,Q-MA to adipic acid, and reacting the adipic acid with the ammonia and hydrogen in the presence of at least one catalyst to form caprolactam.

57. The process of claim 56, wherein the at least one catalyst comprises Ru.

58. The process of claim 53, further comprising: converting the Q,Q-MA to adipic acid; reacting adipic acid with ammonia and hydrogen in the presence of a catalyst; and forming caprolactam therefrom.

* * * * *